United States Patent
Kohno et al.

(10) Patent No.: US 6,963,012 B2
(45) Date of Patent: Nov. 8, 2005

(54) DIARYL ETHER DERIVATIVE, ADDITION SALT THEREOF, AND IMMUNOSUPPRESSANT

(75) Inventors: Yasushi Kohno, Tochigi (JP); Naoki Ando, Gunma (JP); Takahiro Tanase, Tochigi (JP); Kazuhiko Kuriyama, Tochigi (JP); Satoru Iwanami, Ibaraki (JP); Shinji Kudou, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 85 days.

(21) Appl. No.: 10/490,345

(22) PCT Filed: Sep. 25, 2002

(86) PCT No.: PCT/JP02/09864

§ 371 (c)(1),
(2), (4) Date: Mar. 22, 2004

(87) PCT Pub. No.: WO03/029184

PCT Pub. Date: Apr. 10, 2003

(65) Prior Publication Data

US 2004/0242654 A1 Dec. 2, 2004

(30) Foreign Application Priority Data

Sep. 27, 2001 (JP) ........................ 2001-297400
Jul. 25, 2002 (JP) ........................ 2002-216191

(51) Int. Cl.[7] ..................... C07C 217/34; C07C 217/56; C07C 217/64; C07C 255/54; C07C 317/22

(52) U.S. Cl. ................. 564/346; 564/348; 564/351; 564/360; 546/334; 514/357; 514/651; 514/653

(58) Field of Search .................. 564/346, 348, 564/351, 360; 546/334; 514/357, 651, 653

(56) References Cited

U.S. PATENT DOCUMENTS 5,604,229 A    2/1997   Fujita et al.

FOREIGN PATENT DOCUMENTS

EP    1 002 792    5/2000

OTHER PUBLICATIONS

Blank et al., J. of Medicinal Chemistry (1967), vol. 10, No. 4., p. 653–656.*

Jorgensen et al., J. of Medicinal Chemistry (1970), vol. 13, No. 3, p. 367–370.*

* cited by examiner

*Primary Examiner*—Brian Davis
(74) *Attorney, Agent, or Firm*—Wenderoth, Lind & Ponack, L.L.P.

(57) ABSTRACT

The present invention provides diaryl ether derivatives that exhibit significant immunosuppressive effects with less side effects.

The diaryl derivatives of the present invention are represented by the following general formula (1):

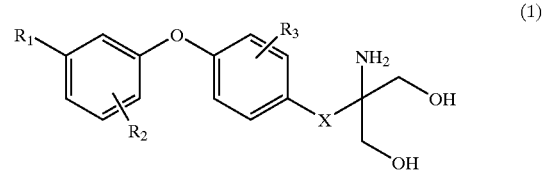

(1)

one example is 2-amino-2-[4-(3-benzyloxyphenoxy)-2-chlorophenyl]propyl-1,3-propanediol.

20 Claims, 4 Drawing Sheets

DIARYL ETHER DERIVATIVE, ADDITION SALT THEREOF, AND IMMUNOSUPPRESSANT

This is a 371 of PCT/JP02/09864, filed Sep. 25, 2002.

TECHNICAL FIELD

The present invention relates to diaryl ether derivatives, salts and hydrates thereof that are useful as an immunosuppressive agent.

TECHNICAL BACKGROUND

Immunosuppressive agents are widely used as a treatment for autoimmune diseases such as rheumatoid arthritis, nephritis, osteoarthritis and systemic lupus erythematosus, chronic inflammatory diseases such as inflammatory bowel disease, and allergic diseases such as asthma and dermatitis. Progress in medicine has led to an increase in the number of tissue and organ transplantations performed each year. In such a situation of modern medicine, having as much control as possible over the rejection following transplantation is a key to successful transplantation. Immunosuppressive agents also play a significant role to this end.

Among immunosuppressors commonly used in organ transplantation are antimetabolites, such as azathioprine and mycophenolate mofetil, calcineurin inhibitors, such as cyclosporin A and tacrolimus, and corticosteroid, such as prednisolone. Some of these drugs are not effective enough while others require continuous monitoring of the blood drug level to avoid renal failure and other serious side effects. Thus, none of conventional immunosuppressive agents are satisfactory in view of efficacy and potential side effects.

Multiple drug combined-therapy, in which different immunosuppressive drugs with different mechanisms of action are used, is becoming increasingly common with the aims of alleviating the side effects of the drugs and achieving sufficient immunosuppressive effects. Also, development of new types of immunosuppressive agents that have completely different mechanisms of action is sought.

In an effort to respond to such demands, the present inventors conducted a search for new types of immunosuppressive agents with main emphasis on 2-amino-1,3-propanediol derivatives.

While the use of 2-amino-1,3-propanediol derivatives as immunosuppressive agents has been disclosed in PCT publication WO94/08943 (YOSHITOMI PHARMACEUTICAL INDUSTRIES, Ltd., TAITO Co., Ltd.) and in Japanese Patent Publication No. Hei 9-2579602 (YOSHITOMI PHARMACEUTICAL INDUSTRIES, Ltd., TAITO Co., Ltd.), it has not been previously known that 2-amino-1,3-propanediol derivatives having a diaryl ether group, which are subjects of the present invention, can serve as an effective immunosuppressor.

DISCLOSURE OF THE INVENTION

Accordingly, it is an objective of the present invention to provide a diaryl ether derivative that exhibits significant immunosuppressive effects with little side effects.

In the course of studies on immunosuppressive agents that have different mechanisms of action from antimetabolites and calcineurin inhibitors, the present inventors discovered that novel diaryl ether derivatives that have a different structure from conventional immunosuppressors exhibit strong immunosuppressive effects. Specifically, the compounds are such that one of the aryl groups includes, at its para-position, a carbon chain with an aminopropanediol group and the other aryl group includes a substituent at its meta-position. This discovery led the present inventors to devise the present invention.

The present invention thus is an immunosuppressive agent containing as an active ingredient at least one of a diaryl ether derivative, a pharmaceutically acceptable salt and hydrate thereof, the diaryl ether derivative represented by the following general formula (1):

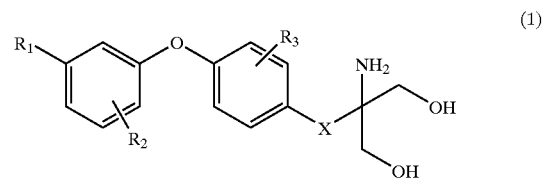

(1)

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is $-(CH_2)_n-$ (n is an integer from 1 to 4), $-OCH_2CH_2-$, or $-CH=CHCH_2-$.

More specifically, the present invention is an immunosuppressive agent containing as an active ingredient at least one of a diaryl ether derivative, a pharmaceutically acceptable salt and hydrate thereof, the diaryl ether derivative represented by the following general formula (1a):

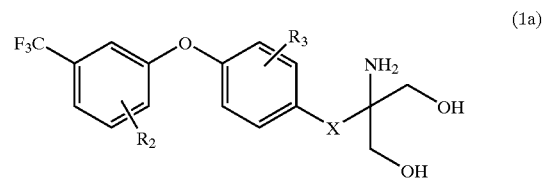

(1a)

wherein $R_2$, $R_3$, and X are the same as defined above.

Furthermore, the present invention is an immunosuppressive agent containing as an active ingredient at least one of a diaryl ether derivative, a pharmaceutically acceptable salt and hydrate thereof, the diaryl ether derivative represented by the following general formula (1b):

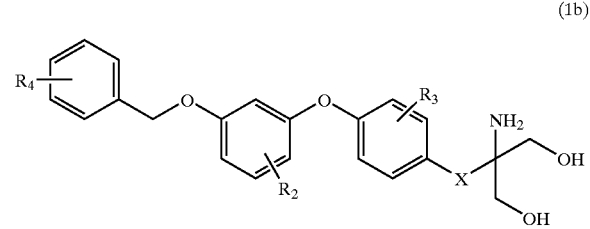

(1b)

wherein $R_2$, $R_3$, and X are the same as defined above; and $R_4$ is hydrogen, halogen, trifluoromethyl, lower alkoxy having 1 to 4 carbon atoms, or lower alkyl having 1 to 7 carbon atoms.

BEST MODE FOR CARRYING OUT THE INVENTION

Figure 1:
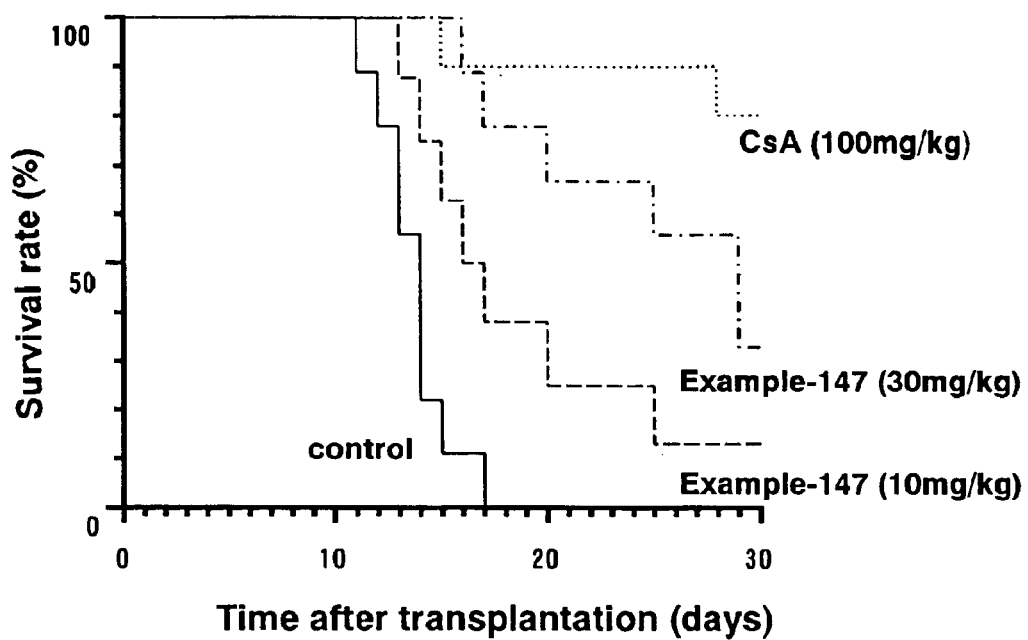
FIG. 1 is a graph showing activities of a test compound in a mouse skin graft model.

The compounds of the general formulae (1), (1a) and (1b) are novel compounds. Examples of the pharmaceutically acceptable salt of the compound of the general formula (1) include acid salts, such as hydrochloride, hydrobromide, acetate, trifluoroacetate, methanesulfonate, citrate, and tartrate.

In the general formula (1), the term 'halogen atom' includes fluorine, chlorine, bromine, and iodine atom. The term 'trihalomethyl group' includes trifluoromethyl and trichloromethyl. The phrase 'lower alkyl group having 1 to 7 carbon atoms' includes straight-chained or branched hydrocarbons having 1 to 7 carbon atoms, such as methyl, ethyl, propyl, isopropyl, butyl, t-butyl, pentyl, hexyl, and heptyl. The phrase 'substituted or unsubstituted phenoxy group' includes those that have, at any position of its benzene ring, a halogen atom, such as fluorine, chlorine, bromine and iodine, trifluoromethyl, lower alkyl having 1 to 4 carbon atoms, or lower alkoxy having 1 to 4 carbon atoms. The term 'aralkyl group' as in 'aralkyl group' or 'aralkyloxy group' includes benzyl, diphenylmethyl, phenethyl, and phenylpropyl. The term 'lower alkyl group' as used in 'lower alkoxyl group having 1 to 4 carbon atoms,' 'lower alkylthio group having 1 to 4 carbon atoms,' 'lower alkylsulfinyl group having 1 to 4 carbon atoms,' or 'lower alkylsulfonyl group having 1 to 4 carbon atoms,' includes straight-chained or branched hydrocarbons having 1 to 4 carbon atoms, such as methyl, ethyl, propyl, isopropyl, and butyl. The phrase 'substituted or unsubstituted aralkyl group' includes those that have, at any position of its benzene ring, a halogen atom, such as fluorine, chlorine, bromine and iodine, trifluoromethyl, lower alkyl having 1 to 4 carbon atoms, or lower alkoxy having 1 to 4 carbon atoms.

According to the present invention, the compounds of the general formula (1) can be produced in the following pathways:

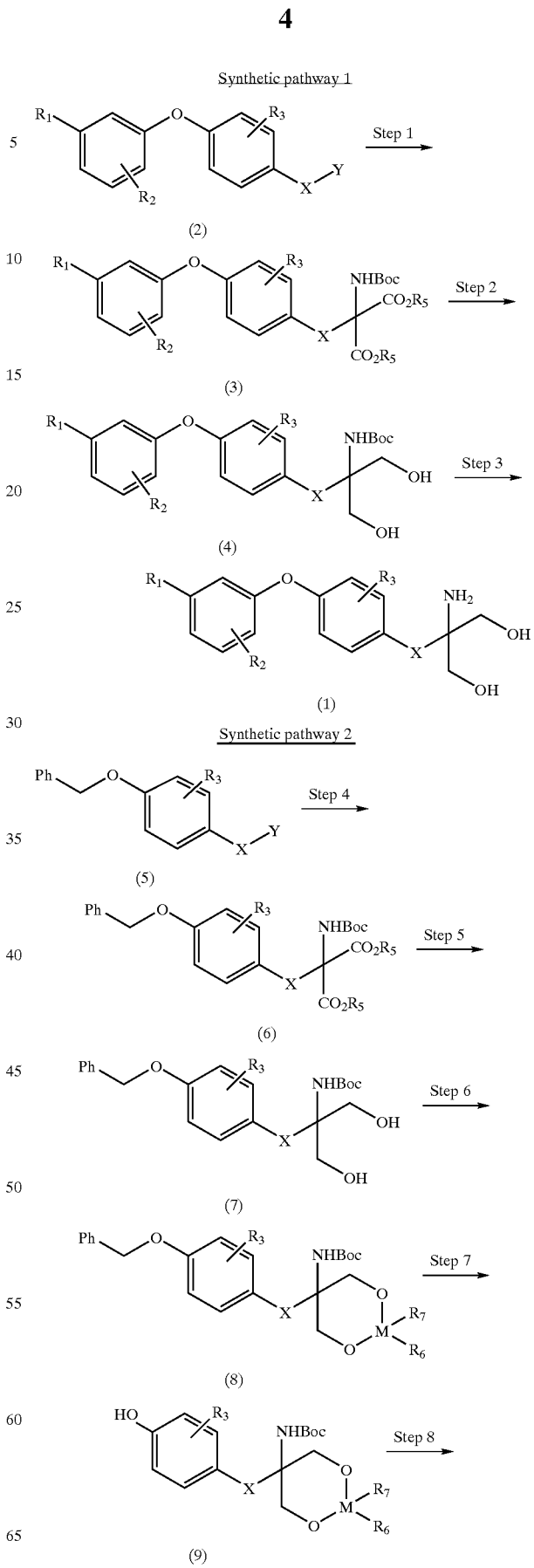

-continued

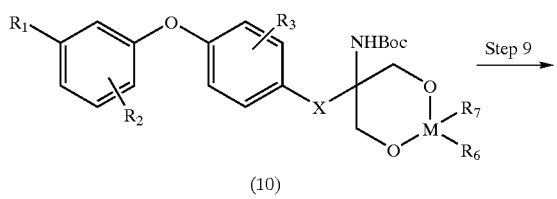

(10)

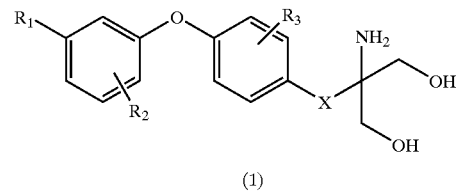

(1)

The compound appearing in the synthetic pathway 1 and represented by the following general formula (3):

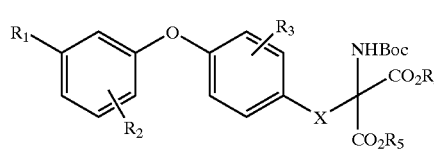

(3)

(wherein $R_5$ is lower alkyl having 1 to 4 carbon atoms; Boc is t-butoxycarbonyl; and $R_1$, $R_2$, $R_3$, and X are the same as described above) can be prepared by reacting a compound of the following general formula (2):

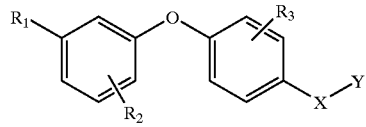

(2)

(wherein Y is chlorine, bromine, or iodine; and $R_1$, $R_2$, $R_3$, and X are as described above) with a compound of the following general formula (11):

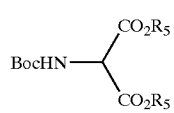

(11)

(wherein $R_5$ and Boc are as described above) in the presence of a base (Step 1).

This reaction can be carried out using a reaction solvent such as 1,4-dioxane, dimethylsulfoxide (DMSO), N,N-dimethylformamide (DMF), tetrahydrofuran (THF), or ethanol at a reaction temperature of 0° C. to reflux temperature, preferably at a temperature of 80° C. to 100° C., in the presence of an inorganic base such as sodium hydride, potassium hydride, sodium alkoxide, and potassium alkoxide.

The compound appearing in the synthetic pathway 1 and represented by the following general formula (4):

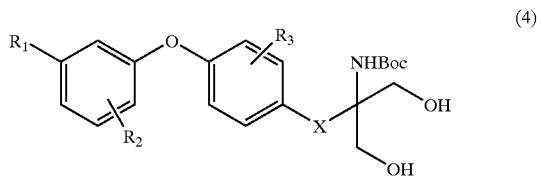

(4)

(wherein $R_1$, $R_2$, $R_3$, $R_4$, X, and Boc are as described above) can be prepared by the reduction of the compound of the general formula (3) (Step 2).

This reaction can be carried out at a reaction temperature of 0° C. to reflux temperature, preferably at room temperature, using an alkylborane derivative, such as borane ($BH_3$) and 9-borabicyclo[3.3.1]nonane (9-BBN), or a metal hydride complex, such as diisobutylaluminum hydride ((iBu)2AlH), sodium borohydride ($NaBH_4$) and lithium aluminum hydride ($LiAlH_4$), preferably lithium borohydride ($LiBH_4$), and using a reaction solvent such as THF, ethanol and methanol.

The compound appearing in the synthetic pathway 1 and represented by the general formula (1):

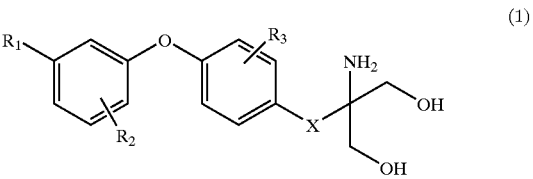

(1)

(wherein $R_1$, $R_2$, $R_3$, and X are as described above) can be prepared by the acidolysis of the compound of the general formula (4) (Step 3).

This reaction can be carried out at a reaction temperature in the range of 0° C. to room temperature in an inorganic or organic acid, such as acetic acid, hydrochloric acid, hydrobromic acid, methanesulfonic acid and trifluoroacetic acid, or in a mixed solvent with an organic solvent such as methanol, ethanol, THF, 1,4-dioxane, and ethyl acetate.

The compound appearing in the synthetic pathway 2 and represented by the following general formula (6):

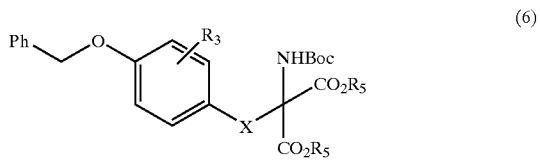

(6)

(wherein $R_3$, $R_5$, X, and Boc are as described above) can be prepared by reacting the compound represented by the following general formula (5):

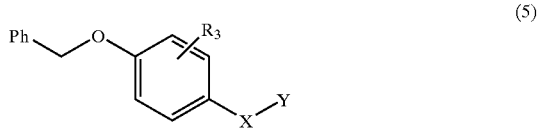

(5)

(wherein R₃, X, and Y are as described above) with the compound of the general formula (11):

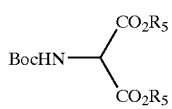  (11)

(wherein R₅, and Boc are as described above) in the presence of a base (Step 4).

This reaction can be carried out using a reaction solvent such as 1,4-dioxane, DMSO, DMF, THF, or ethanol at a reaction temperature in the range of 0° C. to reflux temperature, preferably 80° C. to 100° C., in the presence of an inorganic base such as sodium hydride, potassium hydride, sodium alkoxide, and potassium alkoxide.

The compound appearing in the synthetic pathway 2 and represented by the following general formula (7):

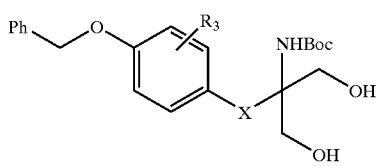  (7)

(where R₃ and X are as described above) can be prepared by the reduction of the compound of the general formula (6) (Step 5).

This reaction can be carried out at a reaction temperature of 0° C. to reflux temperature, preferably at room temperature, using an alkylborane derivative, such as BH₃ and 9-BBN, or a metal hydride complex, such as (iBu)₂AlH, NaBH₄ and LiAlH₄, preferably LiBH₄, and using a reaction solvent such as THF, ethanol, and methanol.

The compound appearing in the synthetic pathway 2 and represented by the following general formula (8):

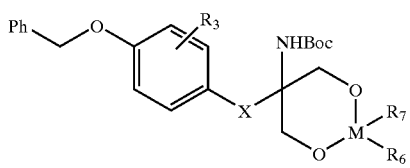  (8)

(wherein M is carbon or silicon; R6 and R7 are each independently hydrogen or lower alkyl having 1 to 4 carbon atoms; and R₃, X and Boc are as described above) can be prepared by reacting the compound of the general formula (7) with a compound of the general formula (12):

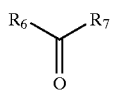  (12)

(where R₆ and R₇ are as described above) or a compound of the general formula (13):

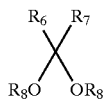  (13)

(wherein R₈ is lower alkyl having 1 to 4 carbon atoms; and R₆ and R₇ are as described above) or a compound of the general formula (14):

  (14)

(wherein R₉ is chlorine or trifluoromethansulfonyloxy; and R₆ and R₇ are as described above) (Step 6).

The reaction between the compound of the general formula (7) and the compound of the general formula (12) or the compound of the general formula (13) can be carried out at a reaction temperature of room temperature to 100° C. either in the presence of a Lewis acid such as zinc chloride or in the presence of an acid catalyst such as camphorsulfonic acid, paratoluenesulfonic acid, and pyridinium paratoluenesulfonic acid, and either in the absence of solvent or in the presence of a reaction solvent such as DMF, THF, and methylene chloride.

The reaction between the compound of the general formula (7) and the compound of the general formula (14) can be carried out at a reaction temperature of 0° C. to 100° C. in the presence of a base such as triethylamine, pyridine, 2,6-lutidine, and imidazole, using a reaction solvent such as DMF, THF, methylene chloride, chloroform, and acetonitrile.

The compound appearing in the synthetic pathway 2 and represented by the general formula (9):

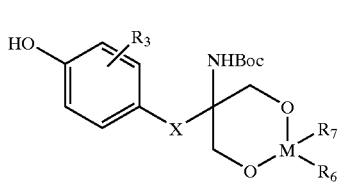  (9)

(wherein R₃, R₆, R₇, X, Boc, and M are as described above) can be prepared by the hydrogenolysis of the compound of the general formula (8) (Step 7).

This reaction can be carried out at a temperature in the range of room temperature to 100° C. in the presence of a reduction catalyst, such as palladium carbon, platinum carbon, platinum oxide, rhodium carbon, and ruthenium carbon, in a solvent, such as ethanol, methanol, THF, DMF, and ethyl acetate, under a hydrogen pressure that is atmospheric pressure or higher.

The compound appearing in the synthetic pathway 2 and represented by the general formula (10):

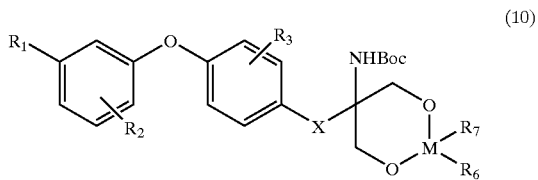
(10)

[wherein $R_1$, $R_2$, $R_3$, $R_6$, $R_7$, X, Boc, and M are as described above] can be prepared by reacting the compound of the general formula (9) with a compound of the general formula (15):

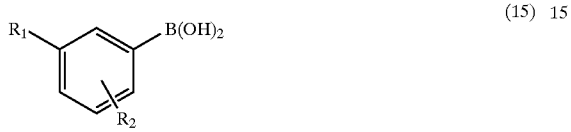
(15)

(wherein $R_1$ and $R_2$ are as described above) in the presence of copper acetate (Step 8).

This reaction can be carried out at room temperature in the presence or absence of a molecular sieve, using copper acetate as a reaction promoter and methylene chloride or chloroform as a solvent, in the presence of a base, such as triethylamine.

The compound appearing in the synthetic pathway 2 and represented by the general formula (1):

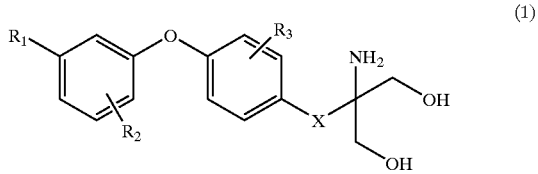
(1)

(wherein R1, R2, R3, and X are as described above) can be prepared by the acidolysis, or desilylation followed by acidolysis, of the compound of the general formula (10) (Step 9).

This reaction can be carried out at a reaction temperature of 0° C. to room temperature in an inorganic or organic acid, such as acetic acid, hydrochloric acid, hydrobromic acid, methanesulfonic acid, trifluoroacetic acid, or in a mixed solution with an organic solvent, such as methanol, ethanol, THF, 1,4-dioxane, and ethyl acetate.

When M in the general formula (10) is a silicon atom, the compound of the general formula (1) can be synthesized by reacting potassium fluoride, cesium fluoride, or tetrabutylammonium fluoride at a temperature of 0° C. to room temperature in a solvent such as THF, DMF, and 1,4-dioxane and then subjecting the resulting compound to the above-described acidolysis.

Of the compounds of the general formula (10), those represented by the general formula (16) in which $R_1$ is a substituted or unsubstituted aralkyloxy group:

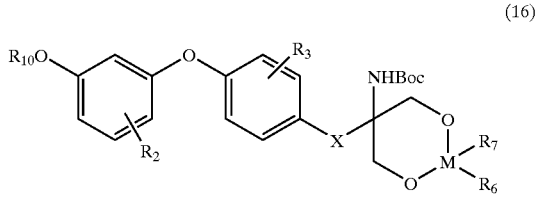
(16)

(wherein $R_{10}$ is substituted or unsubstituted aralkyl; and $R_2$, $R_3$, $R_6$, $R_7$, X, Boc, and M are as described above) can also be prepared by reacting a compound of the general formula (17):

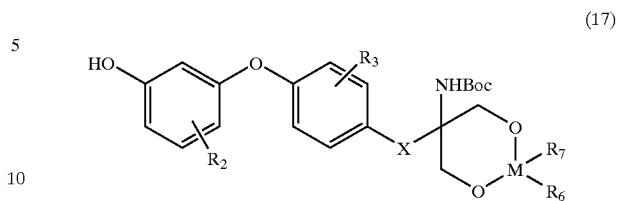
(17)

(wherein $R_2$, $R_3$, $R_6$, $R_7$, X, Boc, and M are as described above) with a compound of the general formula (18):

$R_{10}Y'$ (18)

(wherein Y' is halogen or hydroxy; and $R_{10}$ is as described above).

When Y' is a halogen atom, the reaction can be carried out at a reaction temperature in the range of room temperature to 80° C., using an organic base, such as triethylamine, and pyridine, or an inorganic base, such as sodium hydride, sodium carbonate, and potassium carbonate, and using a reaction solvent, such as THF, DMF, and 1,4-dioxane.

When Y' is a hydroxy, the reaction can be carried out at room temperature in the presence of diethyl azodicarboxylate or triphenylphosphine, using THF as a solvent.

The compound of the general formula (17) can be prepared by the hydrogenolysis of a compound of the general formula (19):

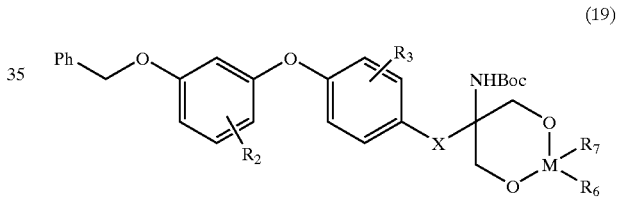
(19)

(wherein $R_2$, $R_3$, $R_6$, $R_7$, X, Boc, and M are as described above).

This reaction can be carried out at a temperature in the range of room temperature to 100° C. in the presence of a reduction catalyst, such as palladium carbon, platinum carbon, platinum oxide, rhodium carbon, and ruthenium carbon, in a solvent, such as ethanol, methanol, THF, DMF, and ethyl acetate, under a hydrogen pressure that is atmospheric pressure or higher.

Of the compounds represented by the general formula (10), those represented by the general formula (20) in which $R_1$ is a substituted or unsubstituted phenoxy group:

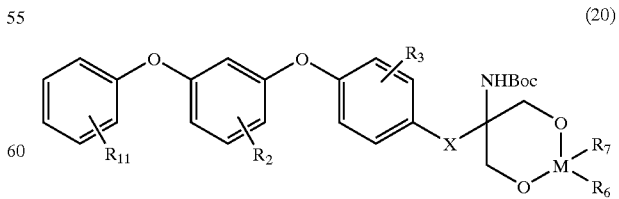
(20)

(wherein $R_{11}$ is hydrogen, halogen, trifluoromethyl, lower alkyl having 1 to 4 carbon atoms, or lower alkoxy having 1 to 4 carbon atoms; and $R_2$, $R_3$, $R_6$, $R_7$, X, Boc, and M are as described above) can be prepared by reacting the compound of the general formula (17) with a compound of the general formula (21):

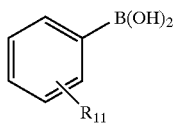

(wherein $R_{11}$ is as described above) in the presence of copper acetate.

This reaction can be carried out preferably at room temperature in the presence or absence of a molecular sieve, using copper acetate as a reaction promoter and methylene chloride or chloroform as a solvent, in the presence of a base, such as triethylamine.

EXAMPLES

The present invention will now be described with reference to examples, which are not intended to limit the scope of the invention in any way.

Reference Example 1
4-(3-benzyloxyphenoxy)-2-chlorobenzaldehyde

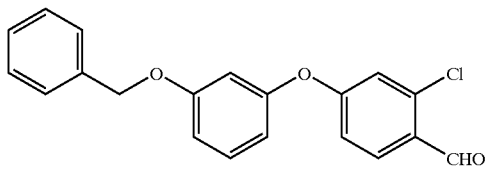

Potassium carbonate (5.53 g) was added to a DMF solution (70 ml) of 2-chloro-4-fluorobenzaldehyde (3.35 g) and 3-benzyloxyphenol (4.23 g) and the solution was stirred for 3 hours while heated to 150° C. The reaction mixture was decanted into water and was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=6:1). In this manner, the desired product (6.73 g) was obtained as a colorless powder.

Reference Examples 2 through 37

Using various phenol derivatives and aldehydes, compounds shown Table 1 were synthesized in the same manner as in Reference Example 1 above.

TABLE 1

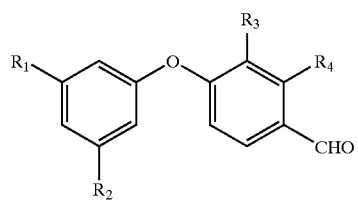

| Reference Example | R1 | R2 | R3 | R4 |
|---|---|---|---|---|
| 2 | $CF_3$ | H | H | H |
| 3 | $CF_3$ | H | MeO | H |

TABLE 1-continued

| Reference Example | R1 | R2 | R3 | R4 |
|---|---|---|---|---|
| 4 | $CF_3$ | H | H | MeO |
| 5 | $CF_3$ | H | Cl | H |
| 6 | $CF_3$ | H | H | Cl |
| 7 | $CF_3$ | H | H | $PhCH_2O$ |
| 8 | $CF_3$ | H | $CF_3$ | H |
| 9 | $CF_3$ | H | H | $CF_3$ |
| 10 | $CF_3$ | $CF_3$ | H | Cl |
| 11 | $CF_3$ | $Ph(CH_2)_2$ | H | H |
| 12 | $Ph(CH_2)_2$ | $Ph(CH_2)_2$ | H | H |
| 13 | $Ph(CH_2)_2$ | H | H | Cl |
| 14 | $Ph(CH_2)_2$ | H | H | $CF_3$ |
| 15 | $Ph(CH_2)_2$ | $Ph(CH_2)_2$ | H | Cl |
| 16 | $Ph(CH_2)_2$ | $Ph(CH_2)_2$ | H | $CF_3$ |
| 17 | $PhCH_2O$ | H | H | H |
| 18 | $PhCH_2O$ | $PhCH_2O$ | H | H |
| 19 | $PhCH_2O$ | H | H | i-Pr |
| 20 | $PhCH_2O$ | $PhCH_2O$ | H | Cl |
| 21 | $PhCH_2O$ | Cl | H | Cl |
| 22 | $PhCH_2O$ | H | H | Br |
| 23 | $PhCH_2O$ | H | H | $CF_3$ |
| 24 | $PhCH_2O$ | H | H | Ph |
| 25 | MeO | $CF_3$ | H | H |
| 26 | MeO | $CF_3$ | H | Cl |
| 27 | t-Bu | H | H | H |
| 28 | MeS | H | H | H |
| 29 | n-$C_5H_{11}$ | H | H | H |
| 30 | n-$C_7H_{15}$ | H | H | H |
| 31 | i-Pr | i-PrO | H | H |
| 32 | i-Pr | i-PrO | H | Cl |
| 33 | i-Pr | i-Pr | H | Cl |
| 34 | Cl | Cl | H | Cl |
| 35 | $PhCH_2S$ | H | H | H |
| 36 | $PhCH_2S$ | H | H | Cl |
| 37 | Me | H | H | H |

Reference Example 38
2-fluoro-4-[(3-trifluoromethyl)phenoxy]benzaldehyde

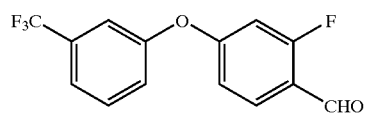

3-(trifluoromethyl)phenylboric acid (1.03 g) and 2-fluoro-4-hydroxybenzaldehyde (760 mg) were dissolved in methylene chloride. While the solution was stirred, copper acetate (985 mg), molecular sieve 4A (800 mg), and triethylamine (3.76 mL) were added. After 6 and 24 hours, the same amount of copper acetate was added and the mixture was stirred for additional 48 hours. The insoluble material was then filtered out and the filtrate was decanted into water and was extracted with ethyl acetate. The organic phase was washed with water and then with a saturated aqueous solution of sodium chloride and was dried with anhydrous magnesium sulfate. Subsequently, the solvent was removed by distillation under reduced pressure and the residue was purified by silica gel column chromatography (hexane:ethyl acetate=7:1, and then 2:1). In this manner, the desired product (265 mg) was obtained as a yellow oil.

Reference Example 39

Ethyl 4'-(3-benzyloxyphenoxy)-2'-chlorocinnamate

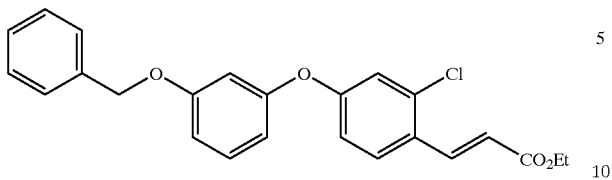

Under argon, 60% sodium hydride (960 mg) was added to a THF solution (150 ml) of ethyl (diethylphosphono)acetate (4.8 mL) at 0° C. and the mixture was stirred for 30 minutes. A THF solution (20 mL) of the compound of Reference Example 1 (6.73 g) was then added dropwise. With the temperature maintained, the mixture was further stirred for 1 hour, followed by addition of water and then extraction with ethyl acetate. The organic phase was washed with water and then with a saturated aqueous solution of sodium chloride and was dried with anhydrous sodium sulfate. The solvent was removed by distillation under reduced pressure and the residue was purified by silica gel column chromatography (hexane:ethyl acetate=6:1). In this manner, the desired product (7.36 g) was obtained as a colorless oil.

Reference Examples 40 through 76

Using the compounds of Reference Examples 2 through 38, the compounds shown in Table 2 below were synthesized in the same manner as in Reference Example 39 above.

TABLE 2

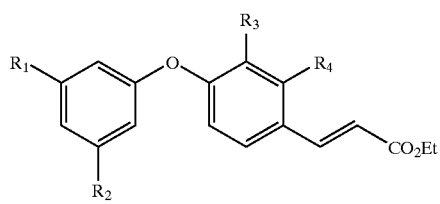

| Reference Example | R1 | R2 | R3 | R4 |
|---|---|---|---|---|
| 40 | $CF_3$ | H | H | H |
| 41 | $CF_3$ | H | MeO | H |
| 42 | $CF_3$ | H | H | MeO |
| 43 | $CF_3$ | H | Cl | H |
| 44 | $CF_3$ | H | H | Cl |
| 45 | $CF_3$ | H | H | $PhCH_2O$ |
| 46 | $CF_3$ | H | $CF_3$ | H |
| 47 | $CF_3$ | H | H | $CF_3$ |
| 48 | $CF_3$ | $CF_3$ | H | Cl |
| 49 | $CF_3$ | $Ph(CH_2)_2$ | H | H |
| 50 | $Ph(CH_2)_2$ | $Ph(CH_2)_2$ | H | H |
| 51 | $Ph(CH_2)_2$ | H | H | Cl |
| 52 | $Ph(CH_2)_2$ | H | H | $CF_3$ |
| 53 | $Ph(CH_2)_2$ | $Ph(CH_2)_2$ | H | Cl |
| 54 | $Ph(CH_2)_2$ | $Ph(CH_2)_2$ | H | $CF_3$ |
| 55 | $PhCH_2O$ | H | H | H |
| 56 | $PhCH_2O$ | $PhCH_2O$ | H | H |
| 57 | $PhCH_2O$ | $PhCH_2O$ | H | Cl |
| 58 | $PhCH_2O$ | H | H | i-Pr |
| 59 | $PhCH_2O$ | Cl | H | Cl |
| 60 | $PhCH_2O$ | H | H | Br |
| 61 | $PhCH_2O$ | H | H | $CF_3$ |
| 62 | $PhCH_2O$ | H | H | Ph |
| 63 | MeO | $CF_3$ | H | H |
| 64 | MeO | $CF_3$ | H | Cl |
| 65 | t-Bu | H | H | H |
| 66 | MeS | H | H | H |

TABLE 2-continued

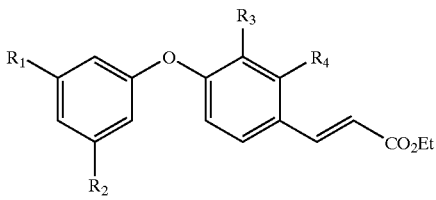

| Reference Example | R1 | R2 | R3 | R4 |
|---|---|---|---|---|
| 67 | n-$C_5H_{11}$ | H | H | H |
| 68 | n-$C_7H_{15}$ | H | H | H |
| 69 | i-Pr | i-PrO | H | H |
| 70 | i-Pr | i-PrO | H | Cl |
| 71 | i-Pr | i-Pr | H | Cl |
| 72 | Cl | Cl | H | Cl |
| 73 | $PhCH_2S$ | H | H | H |
| 74 | $PhCH_2S$ | H | H | Cl |
| 75 | $CF_3$ | H | H | F |
| 76 | Me | H | H | H |

Reference Example 77

Methyl 4'-(3-isobutylphenoxy)cinnamate

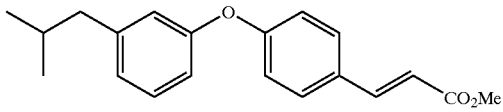

Potassium carbonate (622 mg) was added to a DMF solution (10 ml) of 3-isobutylphenol (451 mg) and methyl 4'-fluorocinnamate (541 mg), and the solution was stirred for 8 hours while heated to 140° C. The reaction mixture was decanted into water and was extracted with ethyl acetate. The organic phase was washed with water and then with a saturated aqueous solution of sodium chloride and was dried with anhydrous sodium sulfate. The solvent was removed by distillation under reduced pressure and the residue was purified by silica gel column chromatography (hexane:ethyl acetate=30:1). In this manner, the desired product (278 mg) was obtained as a yellow oil.

Reference Example 78

Methyl 4'-(3-ethylphenoxy)cinnamate

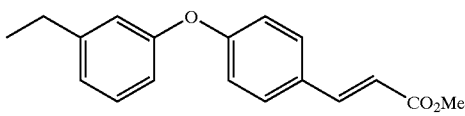

Using 3-ethylphenol and methyl 4'-fluorocinnamate, reactions were carried out in the same manner as in Reference Example 77 above. The desired product was obtained as a yellow oil.

Reference Example 79

Ethyl 4'-[(3-phenoxymethyl)phenoxy]cinnamate

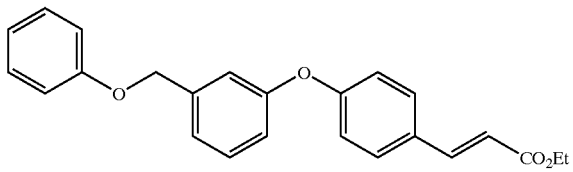

The compound of Reference Example 76 (2.82 g) was dissolved in carbon tetrachloride (50 mL). Following addition of N-bromosuccinimide (2.31 g), the solution was stirred under exposure to light while heated. After 24 hours, the solvent was removed by distillation under reduced pressure, and the residue was extracted with ethyl acetate. The organic phase was washed with water and then with a saturated aqueous solution of sodium chloride and was dried with anhydrous sodium sulfate. The solvent was removed by distillation under reduced pressure and the residue was purified by silica gel column chromatography (hexane:ethyl acetate=6:1). In this manner, ethyl 4'-[(3-bromomethyl)phenoxy]cinnamate (1.30 g) was obtained as a yellow oil. To a DMF solution (25 mL) of the resulting bromide (1.24 g), phenol (380 mg) and potassium carbonate (500 mg) were added, and the mixture was stirred for 3 hours at 60° C. Subsequently, the reaction mixture was decanted into water and was extracted with ethyl acetate. The organic phase was washed with water and then with a saturated aqueous solution of sodium chloride and was dried with anhydrous sodium sulfate. The solvent was removed by distillation under reduced pressure and the residue was purified by silica gel column chromatography (hexane:ethyl acetate=4:1). In this manner, the desired product (1.30 g) was obtained as a colorless oil.

Reference Example 80

Ethyl 4'-[(3-benzyloxy)phenoxy]-2'-chlorodihydrocinnamate

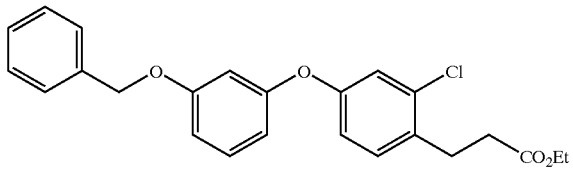

The compound of Reference Example 39 (7.36 g) was dissolved in ethanol (100 mL). While the solution was stirred at 0° C., bismuth chloride (2.84 g) was added. Sodium borohydride (2.72 g) was then added in three portions and the mixture was subsequently stirred for 3 hours at room temperature. Ice water was then added to the reaction mixture and the crystallized inorganic deposits were filtered out through celite. The resulting filtrate was extracted with ethyl acetate. The organic phase was washed with water and then with a saturated aqueous solution of sodium chloride and was dried with anhydrous sodium sulfate. The solvent was removed by distillation under reduced pressure. In this manner, the desired product (7.40 g) was obtained as a colorless oil (Method A).

Reference Example 81

Methyl 4'-(3-isobutylphenoxy)dihydrocinnamate

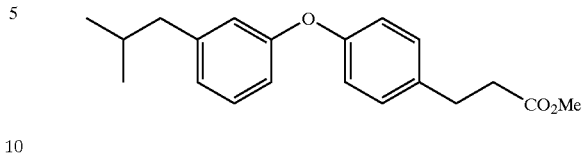

The compound of Reference Example 77 (278 mg) was dissolved in ethanol (5 mL), and 10% Pd/C (70.0 mg) was added to the solution. The resulting mixture was then stirred for 2 hours at room temperature under hydrogen. The catalyst was filtered out and the filtrate was concentrated under reduced pressure to obtain the desired product as a colorless oil (Method B).

Reference Example 82

Methyl 4'-(3-ethylphenoxy)dihydrocinnamate

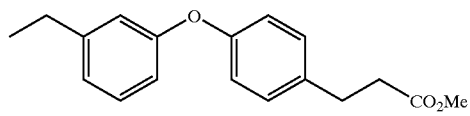

Using the compound of Reference Example 78, reactions were carried out in the same manner as in Reference Example 81 above. In this manner, the desired product was obtained as a colorless oil.

Reference Example 83

Ethyl 3'-chloro-4'-[(3-trifluoromethyl)phenoxy]dihydrocinnamate

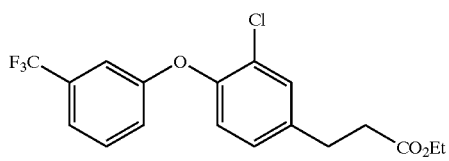

The compound of Reference Example 43 (2.29 g) was dissolved in ethyl acetate (30 mL), and 5% Pd/C-ethylenediamine complex (230 mg) was added to the solution. The resulting mixture was then stirred for 3.5 hours at room temperature under hydrogen. The catalyst was then filtered out and the filtrate was concentrated under reduced pressure to obtain the desired product (2.30 g) as a pale yellow oil (Method C).

Reference Examples 84 through 118

Using the compounds of Reference Examples 40 through 42, 44 through 65, 67 through 75, and 79, reactions were carried out in the same manner as in Reference Examples 80 through 83 above to synthesize compounds as shown in Table 3 below.

TABLE 3

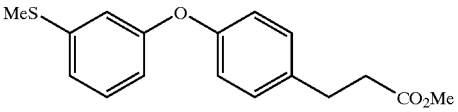

| Reference Example | R1 | R2 | R3 | R4 | Process |
|---|---|---|---|---|---|
| 84 | $CF_3$ | H | H | H | B |
| 85 | $CF_3$ | H | MeO | H | B |
| 86 | $CF_3$ | H | H | MeO | B |
| 87 | $CF_3$ | H | H | Cl | C |
| 88 | $CF_3$ | H | H | $PhCH_2O$ | C |
| 89 | $CF_3$ | H | $CF_3$ | H | B |
| 90 | $CF_3$ | H | H | $CF_3$ | B |
| 91 | $CF_3$ | $CF_3$ | H | Cl | A |
| 92 | $CF_3$ | $Ph(CH_2)_2$ | H | H | B |
| 93 | $Ph(CH_2)_2$ | $Ph(CH_2)_2$ | H | H | B |
| 94 | $Ph(CH_2)_2$ | H | H | Cl | A |
| 95 | $Ph(CH_2)_2$ | H | H | $CF_3$ | B |
| 96 | $Ph(CH_2)_2$ | $Ph(CH_2)_2$ | H | Cl | A |
| 97 | $Ph(CH_2)_2$ | $Ph(CH_2)_2$ | H | $CF_3$ | B |
| 98 | $PhCH_2O$ | H | H | H | A |
| 99 | $PhCH_2O$ | $PhCH_2O$ | H | H | A |
| 100 | $PhCH_2O$ | H | H | i-Pr | A |
| 101 | $PhCH_2O$ | $PhCH_2O$ | H | Cl | A |
| 102 | $PhCH_2O$ | Cl | H | Cl | A |
| 103 | $PhCH_2O$ | H | H | Br | A |
| 104 | $PhCH_2O$ | H | H | $CF_3$ | A |
| 105 | $PhCH_2O$ | H | H | Ph | A |
| 106 | MeO | $CF_3$ | H | H | A |
| 107 | MeO | $CF_3$ | H | Cl | A |
| 108 | t-Bu | H | H | H | B |
| 109 | $n\text{-}C_5H_{11}$ | H | H | H | B |
| 110 | $n\text{-}C_7H_{15}$ | H | H | H | B |
| 111 | i-Pr | i-PrO | H | H | B |
| 112 | i-Pr | i-PrO | H | Cl | C |
| 113 | i-Pr | i-Pr | H | Cl | C |
| 114 | Cl | Cl | H | Cl | A |
| 115 | $PhCH_2S$ | H | H | H | A |
| 116 | $PhCH_2S$ | H | H | Cl | A |
| 117 | $PhOCH_2$ | H | H | H | A |
| 118 | $CF_3$ | H | H | F | B |

Reference Example 119

Ethyl 4'-[(3-t-butyldimethylsiloxy)phenoxy]-2'-chloro-dihydrocinnamate

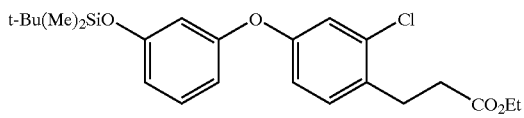

Using the compound of Reference Example 39, reactions were carried out in the same manner as in Reference Example 83 (Method C). The resulting phenol (7.10 g) was dissolved in DMF (80 mL), and imidazole (1.80 g) and t-butyldimethylchlorosilane (3.98 g) were added to the solution. The mixture was then stirred overnight at room temperature. Subsequently, the mixture was decanted into water and was extracted with ethyl acetate. The organic phase was washed with water and then with a saturated aqueous solution of sodium chloride and was dried with anhydrous sodium sulfate. The solvent was removed by distillation under reduced pressure and the residue was purified by silica gel column chromatography (hexane:ethyl acetate=4:1). In this manner, the desired product (8.86 g) was obtained as a colorless oil.

Reference Example 120

Methyl 4'-[(3-methylthio)phenoxy]dihydrocinnamate

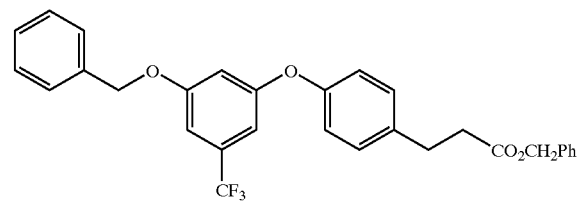

Under argon, the compound of Reference Example 66 (4.07 g) was dissolved in methanol (50 mL). While the solution was stirred at 10° C., magnesium (1.00 g) was added to the solution. With the temperature maintained, the mixture was further stirred for 3 hours, followed by addition of diluted hydrochloric acid and then extraction with ethyl acetate. The organic phase was washed with water and then with a saturated aqueous solution of sodium chloride and was dried with anhydrous sodium sulfate. The solvent was removed by distillation under reduced pressure to obtain the desired product (3.70 g) as a colorless oil.

Reference Example 121

Benzyl 4'-[3-benzyloxy-5-(trifluoromethyl)phenoxy]dihydrocinnamate

The compound of Reference Example 106 (840 mg) was dissolved in methylene chloride (20 mL). While the solution was stirred at 0° C., a 1 mol/L boron tribromide-methylene chloride solution (3.42 mL) was added dropwise. Subsequently, the mixture was stirred overnight at room temperature. Ice water was then added to the reaction mixture and the mixture was extracted with ethyl acetate. The organic phase was sequentially washed with water and a saturated aqueous solution of sodium chloride and was dried with anhydrous sodium sulfate. The solvent was removed by distillation under reduced pressure. In this manner, 4'-(3-trifluoromethyl-5-hydroxyphenoxy)dihydrocinnamate (750 mg) was obtained as a light brown powder. The powder so produced was dissolved in DMF (50 mL), followed by the addition of potassium carbonate (1.04 g) and benzyl bromide (0.602 mL). The mixture was then stirred at room temperature for 8 hours, decanted into ice water, and extracted with ethyl acetate. The organic phase was sequentially washed with water and a saturated aqueous solution of sodium chloride and was then dried with anhydrous sodium sulfate. The solvent was removed by distillation under reduced pressure to obtain the desired product as a brown oil.

Reference Example 122

Ethyl 4'-[3-benzyloxy-5-(trifluoromethyl)phenoxy]-2'-chlorodihydrocinnamate

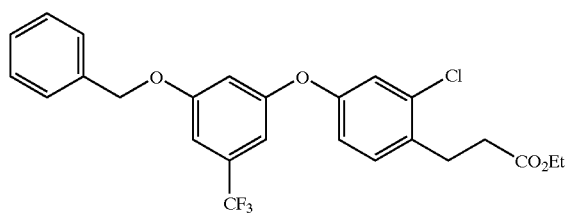

Using the compound of Reference Example 107, 2'-chloro-4'-(3-trifluoromethyl-5-hydroxyphenoxy)dihydrocinnamic acid was obtained in the same manner as in Reference Example 121 above. The cinnamic acid (1.47 g) so obtained was dissolved in ethanol (10 mL). While the solution was stirred at 0° C., thionyl chloride (3 mL) was added dropwise. With the temperature maintained, the solution was stirred for additional 2 hours. The solvent was removed by distillation under reduced pressure and the residue was purified by silica gel column chromatography (hexane:ethyl acetate=10:1 and then 6:1). As a result, ethyl 2'-chloro-4'-(3-trifluoromethyl-5-hydroxyphenoxy)dihydrocinnamate (1.38 g) was obtained as a colorless oil. Using potassium carbonate and benzyl bromide, the resultant ester was subjected to benzyl-etherification as with Reference Example 121 above. In this manner, the desired product was obtained as a colorless oil.

Reference Example 123

4'-[(3-benzyloxy)phenoxy]-2'-chlorodihydrocinnamyl alcohol

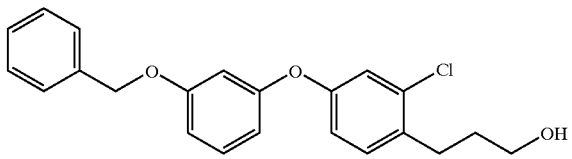

The compound of Reference Example 80 (7.40 g) was dissolved in THF (100 mL). While the solution was stirred at 0° C., lithium aluminum hydride (500 mg) was added. After 10 minutes, a 20% aqueous solution of NaOH was added and the crystallized insoluble inorganic deposits were filtered out through celite. The filtrate was then extracted with ethyl acetate. The organic phase was sequentially washed with water and a saturated aqueous solution of sodium chloride and was dried with anhydrous sodium sulfate. The solvent was removed by distillation under reduced pressure to obtain the desired product (6.37 g) as a colorless oil.

Reference Examples 124 through 163

Using the compounds of Reference Examples 81 through 105 and 108 through 122, the compounds shown in Table 4 below were synthesized in the same manner as in Reference Example 123 above.

TABLE 4

| Reference Example | R1 | R2 | R3 | R4 |
|---|---|---|---|---|
| 124 | CF₃ | H | H | H |
| 125 | CF₃ | H | MeO | H |
| 126 | CF₃ | H | H | MeO |
| 127 | CF₃ | H | Cl | H |
| 128 | CF₃ | H | H | Cl |
| 129 | CF₃ | H | H | PhCH₂O |
| 130 | CF₃ | H | CF₃ | H |
| 131 | CF₃ | H | H | CF₃ |
| 132 | CF₃ | CF₃ | H | Cl |
| 133 | CF₃ | Ph(CH₂)₂ | H | H |
| 134 | CF₃ | H | H | F |
| 135 | Ph(CH₂)₂ | Ph(CH₂)₂ | H | H |
| 136 | Ph(CH₂)₂ | H | H | Cl |
| 137 | Ph(CH₂)₂ | H | H | CF₃ |
| 138 | Ph(CH₂)₂ | Ph(CH₂)₂ | H | Cl |
| 139 | Ph(CH₂)₂ | Ph(CH₂)₂ | H | CF₃ |
| 140 | PhCH₂O | H | H | H |
| 141 | PhCH₂O | PhCH₂O | H | H |
| 142 | tBuMe₂SiO | H | H | Cl |
| 143 | PhCH₂O | H | H | i-Pr |
| 144 | PhCH₂O | PhCH₂O | H | Cl |
| 145 | PhCH₂O | Cl | H | Cl |
| 146 | PhCH₂O | H | H | Br |
| 147 | PhCH₂O | H | H | CF₃ |
| 148 | PhCH₂O | H | H | Ph |
| 149 | PhCH₂O | CF₃ | H | H |
| 150 | PhCH₂O | CF₃ | H | Cl |
| 151 | t-Bu | H | H | H |
| 152 | MeS | H | H | H |
| 153 | n-C₅H₁₁ | H | H | H |
| 154 | n-C₇H₁₅ | H | H | H |
| 155 | i-Pr | i-PrO | H | H |
| 156 | i-Pr | i-PrO | H | Cl |
| 157 | i-Pr | i-Pr | H | Cl |
| 158 | Cl | Cl | H | Cl |
| 159 | PhCH₂S | H | H | H |
| 160 | PhCH₂S | H | H | Cl |
| 161 | Et | H | H | H |
| 162 | i-Bu | H | H | H |
| 163 | PhOCH₂ | H | H | H |

Reference Example 164

4'-[(3-benzyloxy)phenoxy]-2'-chlorodihydrocinnamyl iodide

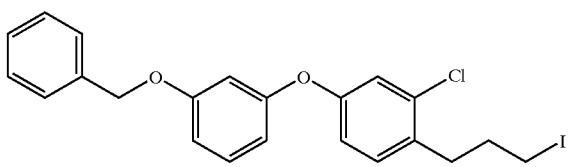

The compound of Reference Example 123 (6.37 g) was dissolved in THF (150 mL). While the solution was stirred at 0° C., imidazole (2.45 g), triphenylphosphine (9.44 g), and iodine (9.14 g) were added. With the temperature maintained, the solution was further stirred for 1 hour.

Subsequently, water was added to the reaction mixture and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=20:1). In this manner, the desired product (7.90 g) was obtained as a colorless oil.

Reference Examples 165 through 204

Using the compounds of Reference Examples 124 through 163, the compounds shown in Table 5 below were synthesized in the same manner as in Reference Example 164 above.

TABLE 5

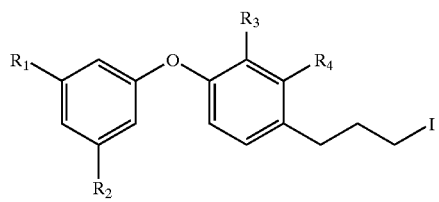

| Reference Example | R1 | R2 | R3 | R4 |
|---|---|---|---|---|
| 165 | CF$_3$ | H | H | H |
| 166 | CF$_3$ | H | MeO | H |
| 167 | CF$_3$ | H | H | MeO |
| 168 | CF$_3$ | H | Cl | H |
| 169 | CF$_3$ | H | H | Cl |
| 170 | CF$_3$ | H | H | PhCH$_2$O |
| 171 | CF$_3$ | H | CF$_3$ | H |
| 172 | CF$_3$ | H | H | CF$_3$ |
| 173 | CF$_3$ | CF$_3$ | H | Cl |
| 174 | CF$_3$ | Ph(CH$_2$)$_2$ | H | H |
| 175 | CF$_3$ | H | H | F |
| 176 | Ph(CH$_2$)$_2$ | Ph(CH$_2$)$_2$ | H | H |
| 177 | Ph(CH$_2$)$_2$ | H | H | Cl |
| 178 | Ph(CH$_2$)$_2$ | H | H | CF$_3$ |
| 179 | Ph(CH$_2$)$_2$ | Ph(CH$_2$)$_2$ | H | Cl |
| 180 | Ph(CH$_2$)$_2$ | Ph(CH$_2$)$_2$ | H | CF$_3$ |
| 181 | PhCH$_2$O | H | H | H |
| 182 | PhCH$_2$O | PhCH$_2$O | H | H |
| 183 | t-BuMe$_2$SiO | H | H | Cl |
| 184 | PhCH$_2$O | H | H | i-Pr |
| 185 | PhCH$_2$O | PhCH$_2$O | H | Cl |
| 186 | PhCH$_2$O | Cl | H | Cl |
| 187 | PhCH$_2$O | H | H | Br |
| 188 | PhCH$_2$O | H | H | CF$_3$ |
| 189 | PhCH$_2$O | H | H | Ph |
| 190 | PhCH$_2$O | CF$_3$ | H | H |
| 191 | PhCH$_2$O | CF$_3$ | H | Cl |
| 192 | t-Bu | H | H | H |
| 193 | MeS | H | H | H |
| 194 | n-C$_5$H$_{11}$ | H | H | H |
| 195 | n-C$_7$H$_{15}$ | H | H | H |
| 196 | i-Pr | i-PrO | H | H |
| 197 | i-Pr | i-PrO | H | Cl |
| 198 | i-Pr | i-Pr | H | Cl |
| 199 | Cl | Cl | H | Cl |
| 200 | PhCH$_2$S | H | H | H |
| 201 | PhCH$_2$S | H | H | Cl |
| 202 | Et | H | H | H |
| 203 | i-Bu | H | H | H |
| 204 | PhOCH$_2$— | H | H | H |

Reference Example 205

4-(3,5-dichlorophenoxy)benzyl bromide

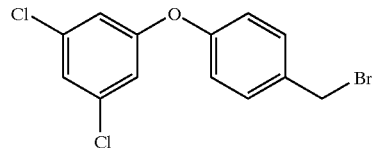

Using 3,5-dichlorophenol and 4-fluorobenzaldehyde, reactions were carried out in the same manner as in Reference Example 1 to obtain 4-(3,5-dichlorophenoxy)benzaldehyde. The subsequent reactions were carried out in the same manner as in Reference Example 123, except that sodium borohydride was used in place of lithium aluminum hydride. This gave 4-(3,5-dichlorophenoxy)benzyl alcohol. The alcohol (2.03 g) and carbon tetrabromide (2.75 g) in methylene chloride (30 mL) were stirred at 0° C., and triphenyl phosphine (2.17 g) was added to the solution. The resulting mixture was stirred for 1 hour at 0° C. and then for 30 minutes at room temperature. Subsequently, the solvent was removed by distillation under reduced pressure and the residue was purified by silica gel column chromatography (hexane:ethyl acetate=20:1). In this manner, the desired product (3.12 g) was obtained as a colorless oil.

Reference Example 206

4'-benzyloxyphenethyl iodide

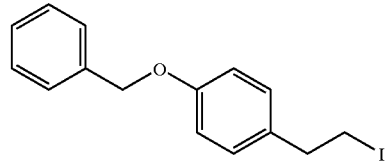

Using ethyl 4'-(benzyloxy)phenyl acetate as a starting material, reactions were carried out in the same manner as in Reference Example 123 to obtain 4'-benzyloxyphenethyl alcohol. Using the alcohol, reactions were then carried out in the same manner as in Reference Example 164 to obtain the desired product as a pale yellow oil.

Reference Example 207

4'-benzyloxy=dihydrocinnamyl iodide

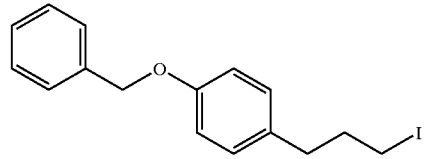

Using 4'-benzyloxydihydrocinnamyl alcohol, reactions were carried out in the same manner as in Reference Example 164 to obtain the desired product as a yellow powder.

Reference Example 208

1-benzyloxy-4-iodobutylbenzene

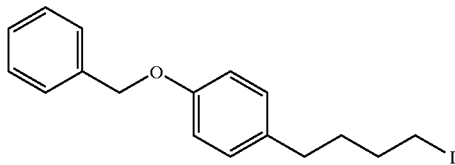

Using methyl 4-(4-benzyloxyphenyl)butyrate as a starting material, reactions were carried out in the same manner as in Reference Example 206 to obtain the desired product as a colorless oil.

Reference Example 209

1-iodopropyl-4-[(3-methanesulfinyl)phenoxy]benzene

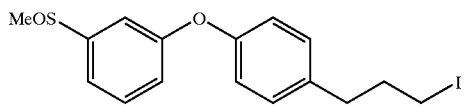

The compound of Reference Example 193 (1.80 g) was dissolved in methylene chloride (30 mL). While the solution was stirred at 0° C., m-chloroperbenzoic acid (770 mg) was added in small portions. With the temperature maintained, the mixture was stirred for 24 hours at room temperature and water was added to the mixture. The resulting mixture was then extracted with ethyl acetate. The organic phase was sequentially washed with a saturated aqueous solution of sodium carbonate and a saturated aqueous solution of sodium chloride and was then dried with anhydrous sodium sulfate. Subsequently, the solvent was removed by distillation under reduced pressure and the residue was purified by silica gel column chromatography (hexane:ethyl acetate=2:1 and then 1:2). In this manner, the desired product (1.29 g) was obtained as a yellow oil.

Reference Example 210

4'-[(3,5-bistrifluoromethyl)phenoxy]cinnamyl chloride

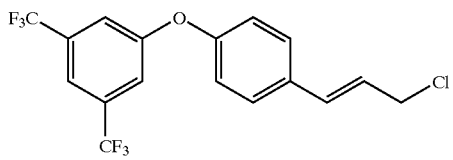

Ethyl 4'-[(3,5-bistrifluoromethyl)phenoxy]cinnamate (500 mg) was dissolved in THF (20 mL). While the solution was stirred at 0° C., a 1 mol/L diisobutylaluminum hydride-toluene solution (3.0 mL) was added. With the temperature maintained, the solution was stirred for 1.5 hours, and a 2 mol/L aqueous solution of sodium hydroxide was added to the solution. The resulting mixture was then extracted with ethyl acetate. The organic phase was sequentially washed with water and a saturated aqueous solution of sodium chloride and was then dried with anhydrous sodium sulfate. Subsequently, the solvent was removed by distillation under reduced pressure and the residue was purified by silica gel column chromatography (hexane:ethyl acetate=3:1). This gave an alcohol (377 mg) as a colorless oil. The alcohol so obtained (296 mg) was dissolved in DMF (5 mL), and lithium chloride (35.0 mg), collidine (0.120 mL), and methanesulfonyl chloride (0.070 mL) were added to the solution at 0° C. With the temperature maintained, the mixture was stirred for 1 hour. Subsequently, the reaction mixture was decanted into water and was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=20:1). In this manner, the desired product (241 mg) was obtained as a colorless powder.

Reference Examples 211 through 219

The compounds were synthesized in the same manner as in Reference Example 1.

TABLE 6

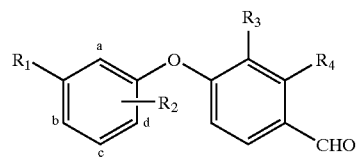

| Reference Example | R1 | R2 | R3 | R4 |
|---|---|---|---|---|
| 211 | Ph(CH$_2$)$_2$ | c-CF$_3$ | H | Cl |
| 212 | PhCH$_2$O | c-H | H | Me |
| 213 | PhCH$_2$O | c-H | H | Et |
| 214 | PhCH$_2$O | c-H | H | SMe |
| 215 | PhO | c-H | H | Cl |
| 216 | CF$_3$ | a-Cl | H | H |
| 217 | CF$_3$ | b-Cl | H | H |
| 218 | CF$_3$ | d-Cl | H | H |
| 219 | CF$_3$ | c-NO$_2$ | H | H |

Reference Example 220

2-fluoro-4-[(3-benzyloxy)phenoxy]benzaldehyde

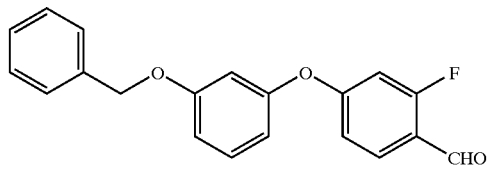

Using 3-benzyloxyphenyboric acid and 2-fluoro-4-hydroxybenzaldehyde, the desired product was obtained as a colorless oil in the same manner as in Reference Example 38.

Reference Examples 221 through 230

Using the compounds of Reference Examples 211 though 220, the compounds were synthesized in the same manner as in Reference Example 39.

TABLE 7

| Reference Example | R1 | R2 | R3 | R4 |
|---|---|---|---|---|
| 221 | $Ph(CH_2)_2$ | $c\text{-}CF_3$ | H | Cl |
| 222 | $PhCH_2O$ | c-H | H | Me |
| 223 | $PhCH_2O$ | c-H | H | Et |
| 224 | $PhCH_2O$ | c-H | H | SMe |
| 225 | PhO | c-H | H | Cl |
| 226 | $CF_3$ | a-Cl | H | H |
| 227 | $CF_3$ | b-Cl | H | H |
| 228 | $CF_3$ | d-Cl | H | H |
| 229 | $CF_3$ | $c\text{-}NO_2$ | H | H |
| 230 | $PhCH_2O$ | c-H | H | F |

Reference Examples 231 through 239

Using the compounds of Reference Examples 221 though 228 and 230, the compounds were synthesized in the same manner as in Reference Examples 80 through 83.

TABLE 8

| Reference Example | R1 | R2 | R3 | R4 |
|---|---|---|---|---|
| 231 | $Ph(CH_2)_2$ | $c\text{-}CF_3$ | H | Cl |
| 232 | $PhCH_2O$ | c-H | H | Me |
| 233 | $PhCH_2O$ | c-H | H | Et |
| 234 | $PhCH_2O$ | c-H | H | SMe |
| 235 | PhO | c-H | H | Cl |
| 236 | $CF_3$ | a-Cl | H | H |
| 237 | $CF_3$ | b-Cl | H | H |
| 238 | $CF_3$ | d-Cl | H | H |
| 239 | $PhCH_2O$ | c-H | H | F |

Reference Examples 240

Ethyl 4'-[3-chloro-5-(trifluoromethyl)phenoxy]dihydrocinnamate

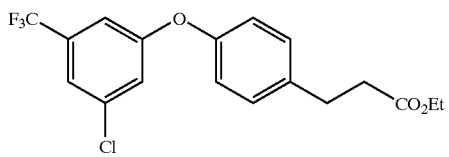

Using the compound of Reference Example 229, reactions were carried out in the same manner as in Reference Example 81 to obtain ethyl 4'-[3-amino-5-(trifluoromethyl)phenoxy]dihydrocinnamate. A MeCN solution (15 mL) of this compound (1.27 g) was added to a MeCN solution (40 mL) of copper chloride (725 mg) and tBuONO (0.51 mL). The mixture was then stirred for 3 hours at room temperature, and water was added to the mixture. The resulting mixture was extracted with ethyl acetate. The organic phase was then washed with water and was dried with anhydrous sodium sulfate. The solvent was removed by distillation under reduced pressure and the residue was purified by silica gel column chromatography (hexane:ethyl acetate=20:1). In this manner, the desired product (1.10 g) was obtained as a pale yellow oil.

Reference Examples 241 through 250

Using the compounds of Reference Examples 231 through 240, the compounds were synthesized in the same manner as in Reference Example 123.

TABLE 9

| Reference Example | R1 | R2 | R3 | R4 |
|---|---|---|---|---|
| 241 | $Ph(CH_2)_2$ | $c\text{-}CF_3$ | H | Cl |
| 242 | $PhCH_2O$ | c-H | H | Me |
| 243 | $PhCH_2O$ | c-H | H | Et |
| 244 | $PhCH_2O$ | c-H | H | SMe |
| 245 | PhO | c-H | H | Cl |
| 246 | $CF_3$ | a-Cl | H | H |
| 247 | $CF_3$ | b-Cl | H | H |
| 248 | $CF_3$ | d-Cl | H | H |
| 249 | $CF_3$ | c-Cl | H | H |
| 250 | $PhCH_2O$ | c-H | H | F |

Reference Examples 251 through 260

Using the compounds of Reference Examples 241 through 250, the compounds were synthesized in the same manner as in Reference Example 164.

TABLE 10

| Reference Example | R1 | R2 | R3 | R4 |
|---|---|---|---|---|
| 251 | $Ph(CH_2)_2$ | $c\text{-}CF_3$ | H | Cl |
| 252 | $PhCH_2O$ | c-H | H | Me |
| 253 | $PhCH_2O$ | c-H | H | Et |
| 254 | $PhCH_2O$ | c-H | H | SMe |
| 255 | PhO | c-H | H | Cl |
| 256 | $CF_3$ | a-Cl | H | H |
| 257 | $CF_3$ | b-Cl | H | H |
| 258 | $CF_3$ | d-Cl | H | H |
| 259 | $CF_3$ | c-Cl | H | H |
| 260 | $PhCH_2O$ | c-H | H | F |

Reference Example 261
4'-[(3-benzyloxy)phenoxy]-2'-chlorophenethyl iodide

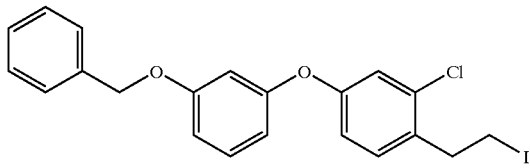

Reference Example 261-1
4'-[(3-benzyloxy)phenoxy]-2'-chlorobenzyl cyanide

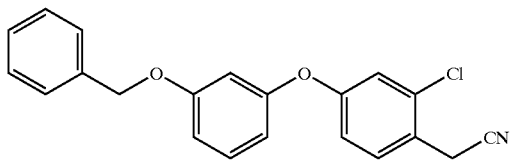

Using the compound of Reference Example 1, reactions were carried out in the same manner as in Reference Example 205 to obtain 4-[(3-benzyloxy)phenoxy]-2-chlorobenzyl bromide as a colorless oil. A DMSO solution (10 mL) of the bromide (1.38 g) was added dropwise to a solution (2 mL water and 5 mL DMSO) of KCN (245 mg) at 90° C., and the mixture was stirred for 10 minutes and then for another 30 minutes at room temperature. Subsequently, ice water was added to the mixture and the mixture was extracted with ethyl acetate. The organic phase was sequentially washed with water and a saturated aqueous solution of sodium chloride and was dried with anhydrous sodium sulfate. The solvent was then concentrated under reduced pressure, and the residue was purified by silica gel column chromatography (hexane:ethyl acetate=5:1). In this manner, the desired product (1.02 g) was obtained as a colorless oil.

Reference Example 261-2
Ethyl 4'-[(3-benzyloxy)phenoxy]-2'-chlorophenylacetate

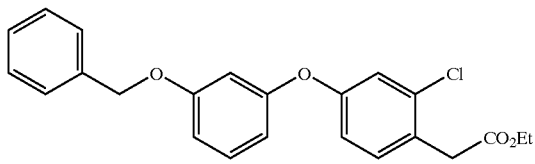

A solution (30 mL) of the compound of Reference Example 261-1 (1.02 g) and potassium hydroxide (819 mg) in a mixed solvent of water (2 mL) and ethanol (30 mL) was refluxed for 12 hours. The solution was made acidic by the addition of hydrochloric acid and was extracted with ethyl acetate. The organic phase was sequentially washed with water and a saturated aqueous solution of sodium chloride and was dried with anhydrous sodium sulfate. The solvent was concentrated under reduced pressure and the resulting concentrate was dissolved in ethanol (10 mL) and thionyl chloride (11.0 mL) was added to the solution. The mixture was subsequently stirred for 1 hour at room temperature. The solvent was removed by distillation and the residue was purified by silica gel column chromatography (hexane:ethyl acetate=10:1). In this manner, the desired product (1.01 g) was obtained as a colorless oil.

Reference Example 261-3
4'-[(3-benzyloxy)phenoxy]-2'-chlorophenethyl iodide

Using the compound of Reference Example 251-2, reactions were carried out in the same manner as in Reference Example 123 to obtain an alcohol. Then, using this alcohol, subsequent reactions are carried out in the same manner as in Reference Example 164 to obtain the desired product as a yellow oil.

Reference Example 262
4-[(3-benzyloxy)phenoxy]-2-chloro-1-iodobutylbenzene

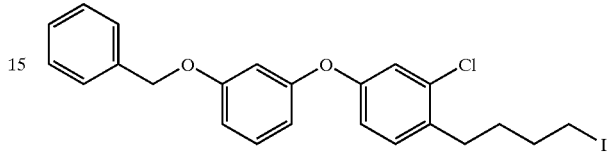

Using the compound of Reference Example 164, reactions were carried out in the same manner as in Reference Example 261 to obtain the desired product as a pale yellow oil.

Example 1
Ethyl 5-[4-(3-benzyloxyphenoxy)-2-chlorophenyl]-2-t-butoxycarbonylamino-2-ethoxycarbonylpentanoate

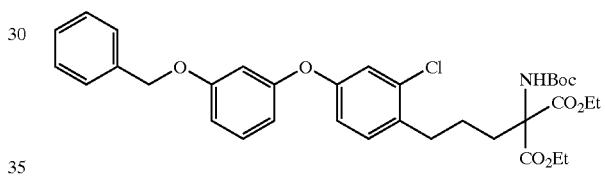

Under argon, sodium=t-butoxide (1.40 g) was added, at room temperature, to a solution of diethyl 2-t-butoxycarbonylaminomalonate (3.60 mL) in a mixed solvent of THF (130 mL) and DMF (20 mL). The resulting mixture was stirred for 30 minutes at 80° C. The temperature was decreased down to room temperature and a THF solution (20 mL) of the compound of Reference Example 164 (6.22 g) was added dropwise. Subsequently, the mixture was refluxed for 5 hours and was decanted into ice water. The resulting mixture was extracted with ethyl acetate. The organic phase was sequentially washed with water and a saturated aqueous solution of sodium chloride and was dried with anhydrous sodium sulfate. The solvent was then removed by distillation under reduced pressure, and the residue was purified by silica gel column chromatography (hexane:ethyl acetate=4:1). In this manner, the desired product (6.84 g) was obtained as a colorless oil.

FABMS: 626 ([M+H]+)

$^1$H-NMR(400 MHz, CDCl$_3$) δ 1.22–1.30(6H, m), 1.42 (9H, s), 1.57(2H, br s), 2.37(2H, br), 2.70(2H, t, J=7.8 Hz), 4.19–4.29(4H, m), 5.03(2H, s), 5.95(1H, bs), 6.57–6.62(2H, m), 6.74(1H, dd, J=8.3, 2.4 Hz), 6.83(1H, dd, J=8.3, 2.4 Hz), 6.98(1H, d, J=2.4 Hz), 7.13(1H, d, J=8.3 Hz), 7.23(1H, t, J=8.3 Hz), 7.33–7.43(5H, m)

Examples 2 through 42

Using the compounds of Reference Examples 165 through 204 and 209, reactions were carried out in the same manner as in Example 1 above to obtain the compounds shown in Table 11 below.

TABLE 11

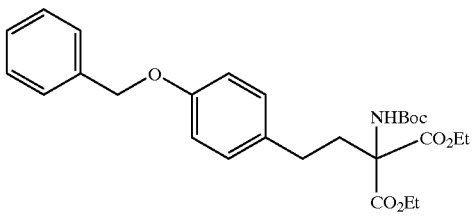

| Example | R1 | R2 | R3 | R4 | Characteristics | Yield (%) |
|---|---|---|---|---|---|---|
| 2 | $CF_3$ | H | H | H | Colorless oil | 100 |
| 3 | $CF_3$ | H | MeO | H | Colorless oil | 100 |
| 4 | $CF_3$ | H | H | MeO | Colorless oil | 100 |
| 5 | $CF_3$ | H | Cl | H | Colorless oil | 100 |
| 6 | $CF_3$ | H | H | Cl | Colorless oil | 100 |
| 7 | $CF_3$ | H | H | $PhCH_2O$ | Colorless oil | 100 |
| 8 | $CF_3$ | H | $CF_3$ | H | Colorless oil | 100 |
| 9 | $CF_3$ | H | H | $CF_3$ | Colorless oil | 92 |
| 10 | $CF_3$ | $CF_3$ | H | Cl | Colorless oil | 89 |
| 11 | $CF_3$ | $Ph(CH_2)_2$ | H | H | Colorless oil | 97 |
| 12 | $CF_3$ | H | H | F | Colorless oil | 100 |
| 13 | $Ph(CH_2)_2$ | $Ph(CH_2)_2$ | H | H | Colorless oil | 95 |
| 14 | $Ph(CH_2)_2$ | H | H | Cl | Colorless oil | 83 |
| 15 | $Ph(CH_2)_2$ | H | H | $CF_3$ | Colorless oil | 90 |
| 16 | $Ph(CH_2)_2$ | $Ph(CH_2)_2$ | H | Cl | Colorless oil | 98 |
| 17 | $Ph(CH_2)_2$ | $Ph(CH_2)_2$ | H | $CF_3$ | Colorless oil | 100 |
| 18 | $PhCH_2O$ | H | H | H | Colorless oil | 95 |
| 19 | $PhCH_2O$ | $PhCH_2O$ | H | H | Colorless oil | — |
| 20 | $PhCH_2O$ | $PhCH_2O$ | H | Cl | Colorless oil | — |
| 21 | $PhCH_2O$ | Cl | H | Cl | Colorless oil | 100 |
| 22 | $PhCH_2O$ | H | H | Br | Colorless oil | 100 |
| 23 | $PhCH_2O$ | H | H | $CF_3$ | Colorless oil | 100 |
| 24 | $PhCH_2O$ | H | H | Ph | Colorless oil | — |
| 25 | $PhCH_2O$ | $CF_3$ | H | H | Colorless oil | 99 |
| 26 | $PhCH_2O$ | $CF_3$ | H | Cl | Colorless oil | 91 |
| 27 | t-Bu | H | H | H | Colorless oil | 64 |
| 28 | MeS | H | H | H | Colorless oil | 83 |
| 29 | $n-C_5H_{11}$ | H | H | H | Colorless oil | 86 |
| 30 | $n-C_7H_{15}$ | H | H | H | Colorless oil | 88 |
| 31 | i-Pr | i-PrO | H | H | Colorless oil | 95 |
| 32 | i-Pr | i-PrO | H | Cl | Colorless oil | 100 |
| 33 | i-Pr | i-Pr | H | Cl | Colorless oil | 66 |
| 34 | Cl | Cl | H | Cl | Colorless oil | 74 |
| 35 | $PhCH_2S$ | H | H | H | Colorless oil | — |
| 36 | $PhCH_2S$ | H | H | Cl | Colorless oil | — |
| 37 | Et | H | H | H | Colorless oil | 100 |
| 38 | i-Bu | H | H | H | Colorless oil | 76 |
| 39 | MeSO | H | H | H | Colorless oil | 100 |
| 40 | $t-BuMe_2SiO$ | H | H | Cl | Colorless oil | 82 |
| 41 | $PhOCH_2$ | H | H | H | Colorless oil | 100 |
| 42 | $PhCH_2O$ | H | H | i-Pr | Colorless oil | — |

The mark "—" means yield is shown in Table 12 as a total yield.

Example 43

Ethyl 2-t-butoxycarbonylamino-2-ethoxycarbonyl-3-[4-(3,5-dichlorophenoxy)phenyl]propionate

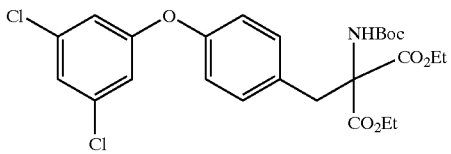

Using the compound of Reference Example 205, reactions were carried out in the same manner as in Example 1 to obtain the desired product as a colorless oil.

$^1$H-NMR(400 MHz, $CDCl_3$) δ 1.28(6H, t, J=7.3 Hz), 1.47(9H, br s), 3.62(2H, br s), 4.19–4.31(4H, m), 5.79(1H, br s), 6.85(2H, d, J=2.0 Hz), 6.92(2H, d, J=8.8 Hz), 7.04–7.08(3H, m)

Example 44

Ethyl 4-[(4-benzyloxy)phenyl]-2-t-butoxycarbonylamino-2-ethoxycarbonylbutyrate

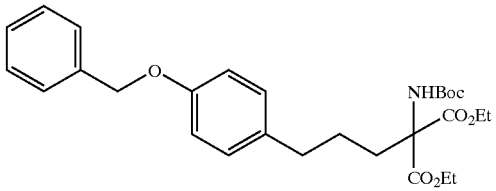

Using the compound of Reference Example 206, reactions were carried out in the same manner as in Example 1 to obtain the desired product as a colorless oil.

$^1$H-NMR(400 MHz, $CDCl_3$) δ 1.23(6H, t, J=7.3 Hz), 1.44(9H, s), 2.44–2.48(2H,m), 2.60(2H, br s), 4.13–4.31 (4H, m), 5.04(2H, s), 5.99(1H, br s), 6.88(2H, d, J=8.8 Hz), 7.07(2H, d, J=8.3 Hz), 7.29–7.44(5H, m)

Example 45

Ethyl 5-[(4-benzyloxy)phenyl]-2-t-butoxycarbonylamino-2-ethoxycarbonylpentanoate

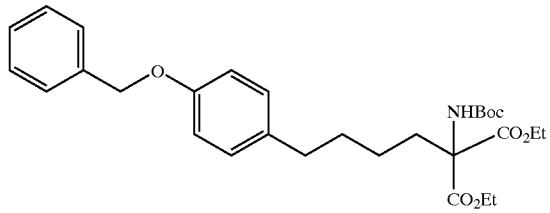

Using the compound of Reference Example 207, reactions were carried out in the same manner as in Example 1 to obtain the desired product as a light yellow oil.

$^1$H-NMR(400 MHz, $CDCl_3$) δ 1.22(6H, t, J=7.1 Hz), 1.42(9H, s), 1.44–1.47(2H,m), 2.31(2H, br s), 2.57(2H, t, J=7.6 Hz), 4.11–4.27(4H, m), 5.03(2H, s), 5.92(1H, br s), 6.88(2H, d, J=8.8 Hz), 7.06(2H, d, J=8.8 Hz), 7.29–7.43(5H, m)

Example 46

Ethyl 6-[(4-benzyloxy)phenyl]-2-t-butoxycarbonylamino-2-ethoxycarbonylhexanoate

Using the compound of Reference Example 208, reactions were carried out in the same manner as in Example 1 to obtain the desired product as a colorless oil.

$^1$H-NMR(400 MHz, $CDCl_3$) δ 1.16–1.24(2H, m), 1.23 (6H, t, J=7.1 Hz), 1.42(9H, s), 1.56–1.63(2H, m), 2.30(2H, br), 2.54(2H, t, J=7.8 Hz), 4:16–4.29(4H, m), 5.03(2H, s), 5.92(1H, br s), 6.88(2H, d, J=8.3 Hz), 7.06(2H, d, J=8.3 Hz), 7.32–7.44(5H, m)

Example 47

Ethyl 5-[4-(3,5-bistrifluoromethylphenoxy)phenyl]-2-t-butoxycarbonylamino-2-ethoxycarbonyl-4-pentenoate

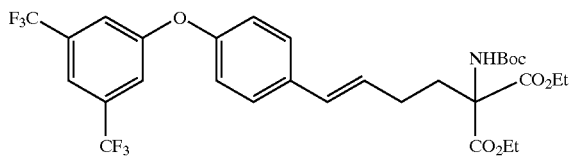

Using the compound of Reference Example 210, reactions were carried out in the same manner as in Example 1 to obtain the desired product as a colorless oil.

$^1$H-NMR(400 MHz, CDCl$_3$) δ 1.27(6H, t, J=7.0 Hz), 1.44(9H, s), 3.20(2H, d, J=7.0 Hz), 4.20–4.32(4H, m), 5.97(1H, br s), 6.02(1H, dt, J=15.9, 7.0 Hz), 6.45(1H, d, J=15.9 Hz), 6.98(2H, d, J=8.5 Hz), 7.36(2H, d, J=8.5 Hz), 7.38(2H, s), 7.57(1H, s)

Example 48

Ethyl 2-t-butoxycarbonylamino-2-ethoxycarbonyl-5-[4-(3-isopropoxyphenoxy)phenyl]pentanoate

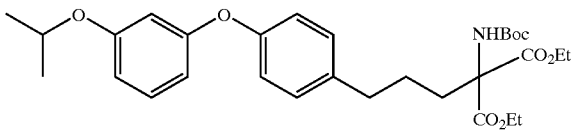

The compound of Example 18 was reduced by catalytic reduction as in Reference Example 81. The resultant phenol (850 mg) was dissolved in DMF (20 mL), and 2-iodopropane (0.2 mL) and potassium carbonate (500 mg) were added to the solution. The mixture was then stirred for 4 hours at 60° C. Subsequently, water was added to the reaction mixture, and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=4:1). In this manner, the desired product (760 mg) was obtained as a colorless oil.

$^1$H-NMR(400 MHz, CDCl$_3$) δ 1.23(6H, t, J=7.3 Hz), 1.31(6H, d, J=5.9 Hz), 1.42(9H, s), 1.45–1.52(2H, m), 2.34(2H, br), 2.61(2H, t, J=7.8 Hz), 4.17–4.27(4H, m), 4.50(1H, heptet, J=5.9 Hz), 5.94(1H, br s), 6.50–6.53(2H, m), 6.59–6.62(1H, m), 6.92(2H, d, J=8.8 Hz), 7.10(2H, d, J=8.8 Hz), 7.18(1H, t, J=8.8 Hz)

Example 49

Ethyl 2-t-butoxycarbonylamino-2-ethoxycarbonyl-5-[4-(3-methanesulfonylphenoxy)phenyl]pentanoate

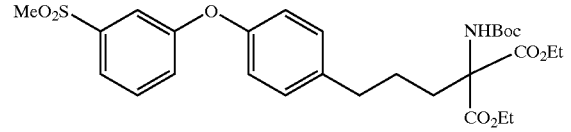

The compound of Example 28 (1.00 g) was dissolved in methylene chloride (30 mL) and m-chloroperbenzoic acid (610 mg) was added to the solution. The mixture was then stirred for 6 hours at room temperature. Subsequently, water was added to the reaction mixture, and the mixture was extracted with ethyl acetate. The organic phase was sequentially washed with water and a saturated aqueous solution of sodium chloride and was dried with anhydrous sodium sulfate. The solvent was removed by distillation under reduced pressure and the residue was purified by silica gel column chromatography (hexane:ethyl acetate=1:1). In this manner, the desired product (610 mg) was obtained as a colorless oil.

$^1$H-NMR(400 MHz, CDCl$_3$) δ 1.24(6H, t, J=7.3 Hz), 1.42(9H, s), 1.47–1.56(2H, m), 2.34(2H, br), 2.64(2H, t, J=7.8 Hz), 3.04(3H, s), 4.18–4.26(4H, m), 5.95(1H, br), 6.95(2H, d, J=8.8 Hz), 7.17(2H, t, J=8.8 Hz), 7.20–7.30(3H, m), 7.47–7.52(2H, m), 7.62(1H, d, J=8.8 Hz)

Example 50

Ethyl 5-[4-(3,5-bistrifluoromethylphenoxy)phenyl]-2-t-butoxycarbonylamino-2-ethoxycarbonylpentanoate

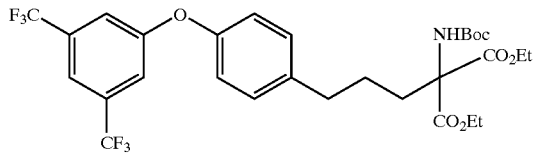

The compound of Example 44 was reduced by catalytic reduction as in Reference Example 81. The resultant phenol was reacted with 3,5-bis(trifluoromethyl)phenylboric acid in the same manner as in Reference Example 38 to obtain the desired product as a pale yellow oil.

$^1$H-NMR(400 MHz, CDCl$_3$) δ 1.24(6H, t, J=7.3 Hz), 1.43(9H, s), 1.47–1.58(4H, m), 2.36(2H, br s), 2.66(2H, t, J=7.3 Hz), 4.18–4.26(4H, m), 5.96(1H, br s), 6.96(2H, d, J=8.3 Hz), 7.20(2H, d, J=8.3 Hz), 7.36(2H, s), 7.55(1H, s)

Example 51

2-[4-(3-benzyloxyphenoxy)-2-chlorophenyl]propyl-2-t-butoxycarbonylamino-1,3-propanediol

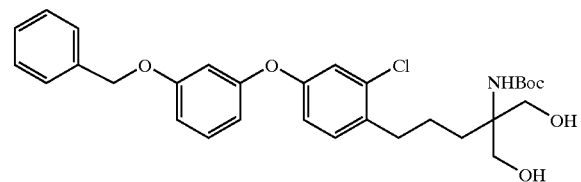

The compound of Example 1 (6.84 g) was dissolved in THF (150 mL). While the solution was stirred at 0° C., lithium borohydride (960 mg) was added to the solution. Ethanol (10 mL) was then added to the mixture and the mixture was stirred for 8 hours as the temperature was gradually increased to room temperature. Subsequently, ice water was added to the mixture and the organic solvent was removed by distillation under reduced pressure. A 10% aqueous solution of citric acid was added to the residue to adjust the pH to 3, and the mixture was extracted with ethyl acetate. The organic phase was sequentially washed with water and a saturated aqueous solution of sodium chloride and was dried with anhydrous sodium sulfate. The solvent was then removed by distillation under reduced pressure.

The residue was purified by silica gel column chromatography (hexane:ethyl acetate=1:1) to obtain the desired product (3.50 g) as a colorless viscous oil.

FABMS: 542([M+H]+)

$^1$H-NMR(400 MHz, CDCl$_3$) δ 1.43(9H, s), 1.66(4H, br s), 2.69(2H, t, J=6.8 Hz), 3.40(2H, br), 3.60(2H, dd, J=11.3, 5.9 Hz), 3.84(2H, dd, J=11.3, 3.8 Hz), 4.92(1H, br s), 5.03(2H, s), 6.59–6.62(2H, m), 6.75(1H, dd, J=8.3, 2.5 Hz), 6.84(1H, dd, J=8.3, 2.5 Hz), 7.00(1H, d, J=2.5 Hz), 7.14(1H, d, J=8.3 Hz), 7.24(1H, t, J=8.3 Hz), 7.31–7.43(5H, m)

Examples 52 through 95

Using the compounds of Examples 2 through 42 and 48 through 50, reactions were carried out in the same manner as in Example 51 above to synthesize the compounds shown in Table 12 below.

Example 96

2-t-butoxycarbonylamino-2-[4-(3,5-dichlorophenoxy)benzyl]-1,3-propanediol

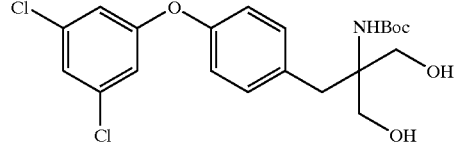

Using the compound of Example 43, reactions were carried out in the same manner as in Example 51 to obtain the desired product as a colorless amorphous.

$^1$H-NMR(400 MHz, CDCl$_3$) δ 1.46(9H, s), 2.94(2H, s), 3.60(2H, d, J=11.7 Hz), 3.75(2H, d, J=11.7 Hz), 4.93(1H, br

TABLE 12

| Example | R1 | R2 | R3 | R4 | Characteristics | Yield (%) |
|---|---|---|---|---|---|---|
| 52 | CF$_3$ | H | H | H | Colorless oil | 71 |
| 53 | CF$_3$ | H | MeO | H | Colorless oil | 76 |
| 54 | CF$_3$ | H | H | MeO | Colorless oil | 45 |
| 55 | CF$_3$ | H | Cl | H | Colorless oil | 58 |
| 56 | CF$_3$ | H | H | Cl | Colorless oil | 68 |
| 57 | CF$_3$ | H | H | PhCH$_2$O | Colorless oil | 64 |
| 58 | CF$_3$ | H | CF$_3$ | H | Colorless oil | 68 |
| 59 | CF$_3$ | H | H | CF$_3$ | Colorless oil | 41 |
| 60 | CF$_3$ | CF$_3$ | H | Cl | Colorless oil | 77 |
| 61 | CF$_3$ | Ph(CH$_2$)$_2$ | H | H | Colorless oil | 80 |
| 62 | CF$_3$ | H | H | F | Colorless oil | 63 |
| 63 | Ph(CH$_2$)$_2$ | Ph(CH$_2$)$_2$ | H | H | Colorless oil | 71 |
| 64 | Ph(CH$_2$)$_2$ | H | H | Cl | Colorless oil | 84 |
| 65 | Ph(CH$_2$)$_2$ | H | H | CF$_3$ | Colorless oil | 72 |
| 66 | Ph(CH$_2$)$_2$ | Ph(CH$_2$)$_2$ | H | Cl | Colorless oil | 61 |
| 67 | Ph(CH$_2$)$_2$ | Ph(CH$_2$)$_2$ | H | CF$_3$ | Colorless oil | 54 |
| 68 | PhCH$_2$O | H | H | H | Colorless oil | 76 |
| 69 | PhCH$_2$O | PhCH$_2$O | H | H | Colorless oil | (45) |
| 70 | PhCH$_2$O | PhCH$_2$O | H | Cl | Colorless oil | (17) |
| 71 | PhCH$_2$O | Cl | H | Cl | Colorless oil | 61 |
| 72 | PhCH$_2$O | H | H | Br | Colorless oil | 61 |
| 73 | PhCH$_2$O | H | H | CF$_3$ | Colorless oil | 83 |
| 74 | PhCH$_2$O | H | H | Ph | Colorless oil | (50) |
| 75 | PhCH$_2$O | CF$_3$ | H | H | Colorless oil | 83 |
| 76 | PhCH$_2$O | CF$_3$ | H | Cl | Colorless oil | 67 |
| 77 | t-Bu | H | H | H | Colorless oil | 78 |
| 78 | MeS | H | H | H | Colorless powder | 56 |
| 79 | n-C$_5$H$_{11}$ | H | H | H | Colorless oil | 98 |
| 80 | n-C$_7$H$_{15}$ | H | H | H | Colorless Oil | 90 |
| 81 | i-Pr | i-PrO | H | H | Colorless oil | 72 |
| 82 | i-Pr | i-PrO | H | Cl | Colorless oil | 82 |
| 83 | i-Pr | i-Pr | H | Cl | Colorless oil | 33 |
| 84 | Cl | Cl | H | Cl | Colorless oil | 79 |
| 85 | PhCH$_2$S | H | H | H | Colorless oil | (20) |
| 86 | PhCH$_2$S | H | H | Cl | Colorless oil | (11) |
| 87 | Et | H | H | H | Colorless oil | 76 |
| 88 | i-Bu | H | H | H | Colorless oil | 92 |
| 89 | MeSO | H | H | H | Colorless oil | 67 |
| 90 | MeSO$_2$ | H | H | H | Colorless amorphous | 78 |
| 91 | i-PrO | H | H | H | Colorless oil | 89 |
| 92 | tBuMe$_2$SiO | H | H | Cl | Colorless oil | 68 |
| 93 | CF$_3$ | CF$_3$ | H | H | Colorless oil | 72 |
| 94 | PhOCH$_2$ | H | H | H | Colorless oil | 64 |
| 95 | PhCH$_2$O | H | H | i-Pr | Colorless oil | (62) |

In the parentheses, shown is the total, yield of the two steps.

s), 6.87(2H, d, J=2.0 Hz), 6.98(2H, d, J=8.8 Hz), 7.08(1H, t, J=2.0 Hz), 7.26(2H, d, J=8.8 Hz)

Example 97
2-(4-benzyloxyphenyl)ethyl-2-t-butoxycarbonylamino-1,3-propanediol

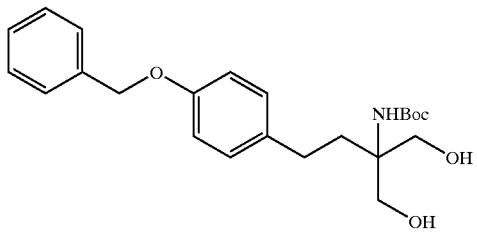

Using the compound of Example 44, reactions were carried out in the same manner as in Example 51 to obtain the desired product as a colorless powder.
$^1$H-NMR(400 MHz, CDCl$_3$) δ 1.45(9H, s), 1.83–1.88(2H, m), 2.54–2.59(2H, m), 3.39(2H, br s), 3.64(2H, d, J=11.2 Hz), 3.88(2H, d, J=11.2 Hz), 5.01(1H, br s), 5.03(2H, s), 6.90(2H, d, J=8.3 Hz), 7.10(2H, d, J=8.3 Hz), 7.30–7.44(5H, m)

Example 98
2-[(4-benzyloxy)phenyl]propyl-2-t-butoxycarbonylamino-1,3-propanediol

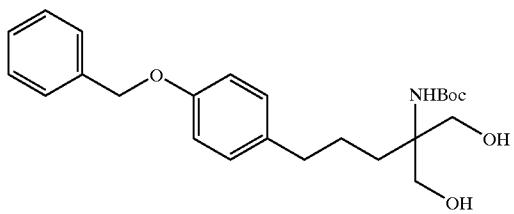

Using the compound of Example 45, reactions were carried out in the same manner as in Example 51 to obtain the desired product as a pale yellow oil.
$^1$H-NMR(400 MHz, CDCl$_3$) δ 1.43(9H, s), 1.50–1.70(4H, m), 2.52–2.57(2H, m), 3.57(2H, d, J=11.2 Hz), 3.82(2H, d, J=11.2 Hz), 4.86(1H, br s), 5.04(2H,s), 6.90(2H, d, J=8.8 Hz), 7.08(2H, d, J=8.8 Hz), 7.31–7.44(5H, m)

Example 99
2-[(4-benzyloxy)phenyl]butyl-2-t-butoxycarbonylamino-1,3-propanediol

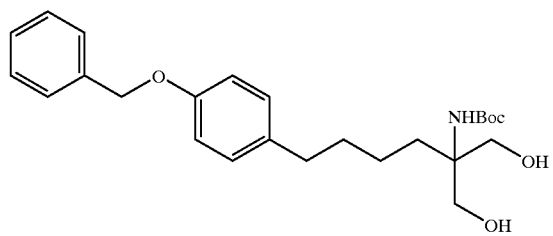

Using the compound of Example 46, reactions were carried out in the same manner as in Example 51 to obtain the desired product as a colorless oil.
$^1$H-NMR(400 MHz, CDCl$_3$) δ 1.27–1.35(2H, m), 1.43 (9H, s), 1.54–1.63(4H, m), 2.56(2H, t, J=7.6 Hz), 3.41(2H, br s), 3.58(2H, d, J=11.7 Hz), 3.82(2H, d, J=11.7 Hz), 4.88(1H, br s), 5.04(2H, s), 6.89(2H, d, J=8.8 Hz), 7.07(2H, d, J=8.8 Hz), 7.33–7.43(5H, m)

Example 100
2-[4'-(3,5-bistrifluoromethylphenoxy)cinnamyl]-2-t-butoxycarbonylamino-1,3-propanediol

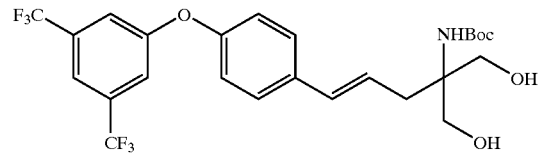

Using the compound of Example 47, reactions were carried out in the same manner as in Example 51 to obtain the desired product as a colorless amorphous.
$^1$H-NMR(400 MHz, CDCl$_3$) δ 1.44(9H, s), 2.55(2H, d, J=7.8 Hz), 3.65(2H, d, J=11.2 Hz), 3.78(2H, br), 3.85(2H, d, J=11.2 Hz), 5.12(1H, s), 6.20(1H, dt, J=16.1, 7.8 Hz), 6.51(1H, d, J=16.1 Hz), 7.01(2H, d, J=8.3 Hz) 7.38(2H,s), 7.39(2H, d, J=8.3 Hz), 7.57(1H, s)

Example 101
5-[(4-benzyloxy)phenyl]propyl-5-t-butoxycarbonylamino-2,2-di-t-butyl-1,3,2-dioxasilane

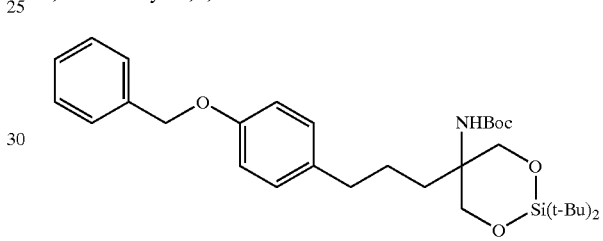

At 0° C., a methylene chloride solution (5 mL) of di-t-butylsilyl bistrifluoromethanesulfonate (1.67 g) was added to a DMF solution (30 mL) of the compound of Example 98 (1.50 g) and 2,6-lutidine (0.841 mL). With the temperature maintained, the mixture was stirred for 1 hour. Subsequently, the mixture was decanted into ice water and was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=20:1) to obtain the desired product (1.67 g) as a colorless powder.
$^1$H-NMR(400 MHz, CDCl$_3$) δ 1.04(9H, s), 1.06(9H, s), 1.42(9H, s), 1.46–1.56(4H, br s), 2.51(2H, t, J=6.8 Hz), 3.88(2H, d, J=11.2 Hz), 4.22(2H, d, J=11.2 Hz), 4.90(1H, br s), 5.04(2H, s), 6.89(2H, d, J=8.3 Hz), 7.06(2H, d, J=8.3 Hz), 7.32–7.44(5H, m)

Example 102
5-t-butoxycarbonylamino-2,2-di-t-butyl-5-(4-hydroxyphenyl)propyl-1,3,2-dioxasilane

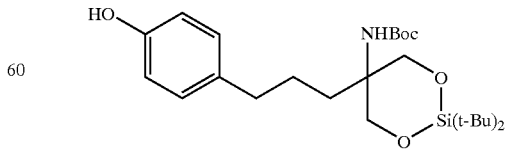

Using the compound of Example 101, catalytic reduction was carried out in the same manner as in Reference Example 81 to obtain the desired product as a pale brown amorphous.

¹H-NMR(400 MHz, CDCl₃) δ 1.04(9H, s), 1.06(9H, s), 1.43(9H, s), 1.47–1.61(4H, m), 2.49(2H, t, J=6.8 Hz), 3.88 (2H, d, J=11.3 Hz), 4.22(2H, d, J=11.3 Hz), 4.88(1H, br s), 4.91(1H, br s), 6.74(2H, d, J=8.3 Hz), 6.99(2H, d, J=8.3 Hz)

Example 103
5-t-butoxycarbonylamino-2,2-di-t-butyl-5-(4-hydroxyphenyl)ethyl-1,3,2-dioxasilane

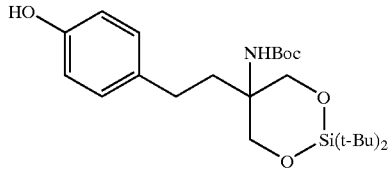

Using the compound of Example 97, reactions were carried out in the same manner as in Examples 101 and 102 to obtain the desired product as a colorless powder.

¹H-NMR(400 MHz, CDCl₃) δ 1.06(9H, s), 1.07(9H, s), 1.46(9H, s), 1.79(2H, m), 2.44–2.50(2H, m), 3.93(2H, d, J=11.2 Hz), 4.26(2H, d, J=11.2 Hz), 4.92(1H, br s), 5.01(1H, br s), 6.73(2H, d, J=8.3 Hz), 7.01(2H, d, J=8.3 Hz)

Example 104
5-t-butoxycarbonylamino-2,2-di-t-butyl-5-(4-hydroxyphenyl)butyl-1,3,2-dioxasilane

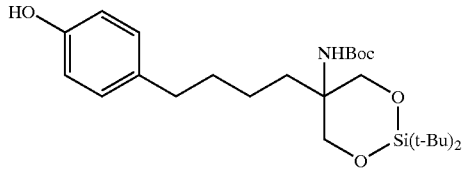

Using the compound of Example 99, reactions were carried out in the same manner as in Examples 101 and 102 to obtain the desired product as a colorless amorphous.

¹H-NMR(400 MHz, CDCl₃) δ 1.05(9H, s), 1.07(9H, s), 1.20–1.30(2H, m), 1.42(9H, s), 1.50–1.60(4H, m), 2.51(2H, t, J=7.6 Hz), 3.89(2H, d, J=11.2 Hz), 4.22(2H, d, J=11.2 Hz), 4.78(1H, br s), 4.91(1H, br s), 6.73(2H, d, J=8.3 Hz), 7.00(2H, d, J=8.3 Hz)

Example 105
5-t-butoxycarbonylamino-5-[4-(3-hydroxyphenoxy)phenyl]propyl-2,2-dimethyl-1,3-dioxane

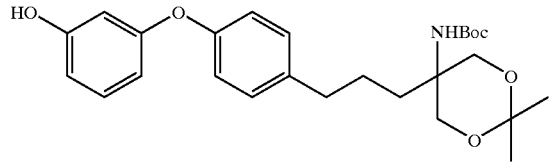

2,2-dimethoxypropane (7.4 mL) and paratoluenesulfonic acid (100 mg) were added to a DMF solution (30 mL) of the compound of Example 68 (3.00 g). The mixture was stirred for 6 hours while heated to 80° C. Subsequently, the mixture was decanted into water and was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=3:1) to obtain the acetonide (2.68 g) as a colorless powder. The resultant acetonide was reduced by catalytic reduction as in Reference Example 81 to obtain the desired product (2.23 g) as a colorless powder.

¹H-NMR(400 MHz, CDCl₃) δ 1.40(3H, s), 1.42(12H, s), 1.54–1.69(4H, m), 2.61(2H, t, J=7.8 Hz), 3.63(2H, d, J=11.2 Hz), 3.87(2H, d, J=11.2 Hz), 4.86(1H,br), 5.29(1H, br s), 6.32(1H, br s), 6.52(1H, dd, J=8.3, 2.4 Hz), 6.57(1H, dd, J=8.3, 2.4 Hz), 6.95(2H, d, J=8.3 Hz), 7.13(2H, d, J=8.3 Hz), 7.16(1H, t, J=8.3 Hz)

Example 106
5-t-butoxycarbonylamino-5-[2-chloro-4-(3-hydroxyphenoxy)phenyl]propyl-2,2-dimethyl-1,3-dioxane

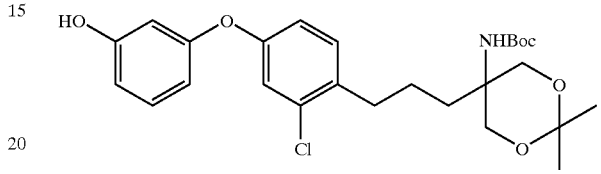

Using the compound of Example 51, reactions were carried out in the same manner as in Example 105 to obtain the desired product as a colorless powder.

Alternatively, an acetonide (3.21 g) obtained by using the compound of Example 92 was dissolved in THF (100 mL). While the solution was stirred at 0° C., a 1 mol/L tetrabutylammoniumfluoride-THF solution (10 mL) was added dropwise. After 10 minutes, water was added to the mixture and the mixture was extracted with ethyl acetate. The organic phase was sequentially washed with water and a saturated aqueous solution of sodium chloride and was dried with anhydrous sodium sulfate. The solvent was then removed by distillation under reduced pressure to obtain the desired product (2.60 g).

FABMS: 492 ([M+H]+)

¹H-NMR(400 MHz, CDCl₃) δ 1.41(3H, s), 1.42(12H, s), 1.55–1.73(4H, m), 2.70(2H, t, J=7.3 Hz), 3.66(2H, d, J=11.7 Hz), 3.88(2H, d, J=11.7 Hz), 4.89(1H,br), 5.97(1H, br), 6.40(1H, br s), 6.56(1H, dd, J=8.3, 2.4 Hz), 6.62(1H, dd, J=8.3, 2.4 Hz), 6.86(1H, dd, J=8.3, 2.4 Hz), 7.01(1H, d, J=2.4 Hz), 7.14(1H, d, J=8.3 Hz), 7.18(1H, d, J=8.3 Hz)

Example 107
5-t-butoxycarbonylamino-5-[2-chloro-4-(3-(3,5-dichlorobenzyloxy)phenoxy)phenyl]propyl-2,2-dimethyl-1,3-dioxane

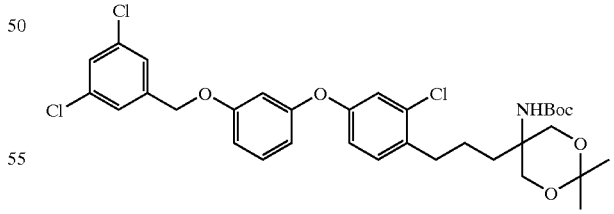

Diethyl azodicarboxylate (0.31 mL) was added to a THF solution (5 mL) containing the compound of Example 106 (650 mg), 3,5-dichlorobenzyl alcohol (350 mg), triphenylphosphine (530 mg). The mixture was stirred for 18 hours. Subsequently, water was added to the mixture and the mixture was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=3:1) to obtain the desired product (440 mg) as a colorless powder.

$^1$H-NMR(400 MHz, CDCl$_3$) δ 1.41(3H, s), 1.42(3H, s), 1.43(9H, s), 1.54–1.60(2H, m), 1.75(2H, br), 2.69(2H, t, J=7.3 Hz), 3.66(2H, d, J=11.7 Hz), 3.88(2H, d, J=11.7 Hz), 4.89(1H, br), 4.98(2H, s), 6.58–6.64(2H, m), 6.70(1H, dd, J=8.3, 2.4 Hz), 6.84(1H, dd, J=8.3, 2.4 Hz), 7.00(1H, d, J=2.4 Hz), 7.15(1H, d, J=8.3 Hz), 7.22–7.32(4H, m)

Example 108
5-t-butoxycarbonylamino-2,2-dimethyl-5-[4-(3-phenoxy)phenoxyphenyl]propyl-1,3-dioxane

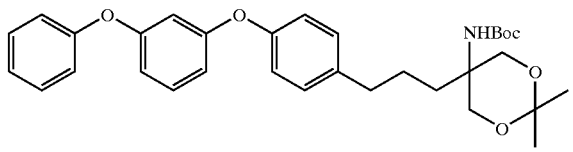

The compound of Example 105 was reacted with phenylboric acid in the same manner as in Reference Example 38 to obtain the desired product as a colorless powder.

$^1$H-NMR(400 MHz, CDCl$_3$) δ 1.40(3H, s), 1.42(3H, s), 1.43(9H, s), 1.54–1.61(2H, m), 1.70(2H, br), 2.58(2H, t, J=7.3 Hz), 3.64(2H, d, J=11.2 Hz), 3.89(2H, d, J=11.2 Hz), 4.87(1H,br), 6.66–6.71(3H, m), 6.94(2H, d, J=8.3 Hz), 7.02 (2H, d, J=8.3 Hz), 7.11–7.13(3H, m), 7.21(1H, t, J=8.3 Hz), 7.34(2H, t, J=8.3 Hz)

Example 109
5-t-butoxycarbonylamino-2,2-di-t-butyl-5-[4-(3-isopropylphenoxy)phenyl]propyl-1,3,2-dioxasilane

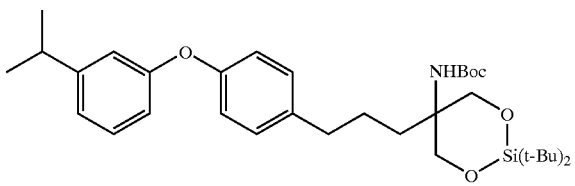

The compound of Example 102 (200 mg), 3-isopropylphenylboric acid (141 mg), anhydrous copper acetate (II) (97.4 mg), and molecular sieve powder-4A (400 mg) were suspended in dichloromethane (5 mL). Triethylamine (120 μL) was then added to the suspension and the suspension was stirred for 8 hours at room temperature. Subsequently, additional 3-isopropylphenylboric acid (141 mg) and triethylamine (120 μL) were added and the resulting mixture was further stirred overnight at room temperature. The reaction mixture was diluted with a mixture of hexane and ethyl acetate (hexane:ethyl acetate=2:1) and was filtered through celite to remove insoluble materials. The filtrate was concentrated under reduced pressure and the residue was purified by silica gel column chromatography (hexane:ethyl acetate=30:1) to obtain the desired product (188 mg) as a colorless oil.

$^1$H-NMR(400 MHz, CDCl$_3$) δ 1.05(9H, s), 1.07(9H, s), 1.23(6H, d, J=6.8 Hz), 1.43(9H, s), 1.55(4H, br s), 2.55(2H, t, J=7.1 Hz), 2.84–2.91(1H, m), 3.89(2H, d, J=11.7 Hz), 4.23(2H, d, J=11.7 Hz), 4.91(1H, br s), 6.75–6.79(1H, m), 6.89–6.91(1H, m), 6.91(2H, d, J=8.8 Hz), 6.95(1H, d, J=7.8 Hz), 7.09(2H, d, J=8.8 Hz), 7.22(1H, t, J=7.8 Hz)

Examples 110 through 125

The compound of Example 102 was reacted with different phenylboric acids in the same manner as in Example 109 described above to synthesize the compounds shown in Table 13 below.

TABLE 13

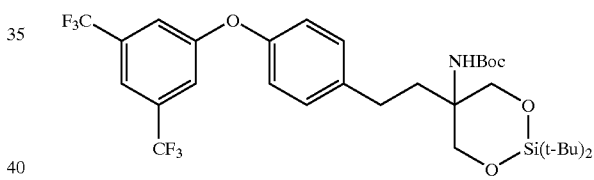

| Example | R1 | R2 | Yield (%) | Characteristics |
|---|---|---|---|---|
| 110 | F | H | 60 | Colorless oil |
| 111 | Cl | H | 61 | Colorless oil |
| 112 | Br | H | 59 | Colorless oil |
| 113 | Me | H | 84 | Colorless oil |
| 114 | Ph | H | 74 | Colorless amorphous |
| 115 | MeO | H | 69 | Colorless oil |
| 116 | EtO | H | 76 | Colorless oil |
| 117 | CF$_3$O | H | 68 | Colorless oil |
| 118 | CH$_2$OH | H | 41 | Colorless powder |
| 119 | Ac | H | 80 | Pale yellow oil |
| 120 | NO$_2$ | H | — | Pale yellow powder |
| 121 | CN | H | 44 | Colorless oil |
| 122 | F | F | 79 | Colorless oil |
| 123 | Cl | Cl | 60 | Pale yellow oil |
| 124 | CF$_3$ | CF$_3$ | 83 | Colorless oil |
| 125 | CHO | H | 74 | Colorless oil |

The mark "—" means yield is shown in Table 15 as a total yield.

Example 126
5-t-butoxycarbonylamino-2,2-di-t-butyl-5-[4-(3,5-bistrifluoromethylphenoxy)phenyl]ethyl-1,3,2-dioxasilane

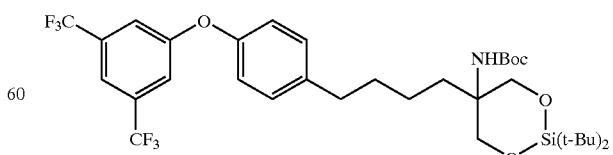

The compound of Example 103 was reacted with 3,5-bis(trifluoromethyl)phenylboric acid in the same manner as in Example 109 to obtain the desired product as a colorless powder.

$^1$H-NMR(400 MHz, CDCl$_3$) δ 1.07(9H, s), 1.09(9H, s), 1.47(9H, s), 1.87(2H, m), 2.55–2.60(2H, m), 3.97(2H, d, J=11.2 Hz), 4.28(2H, d, J=11.2 Hz), 5.05(1H, br s), 6.96(2H, d, J=8.3 Hz), 7.21(2H, d, J=8.3 Hz), 7.34(2H, s), 7.54(1H, s)

Example 127
5-t-butoxycarbonylamino-2,2-di-t-butyl-5-[4-(3,5-bistrifluoromethylphenoxy)phenyl]butyl-1,3,2-dioxasilane The compound of Example 104 was reacted with 3,5-bis(trifluoromethyl)phenylboric acid in the same manner as in Example 109 to obtain the desired product as a colorless oil.

¹H-NMR(400 MHz, CDCl₃) δ 1.05(9H, s), 1.08(9H, s), 1.25–1.31(2H, m), 1.42(9H, s), 1.55–1.63(4H, m), 2.61(2H, t, J=7.8 Hz), 3.91(2H, d, J=11.2 Hz), 4.23(2H, d, J=11.2 Hz), 4.92(1H, br s), 6.95(2H, d, J=8.3 Hz), 7.19(2H, d, J=8.3 Hz), 7.36(2H, s), 7.54(1H, s)

Examples 128 and 129

The compounds of Examples 103 and 104 were reacted with 3,5-dichlorophenylboric acid in the same manner as in Example 109 to obtain the following products:

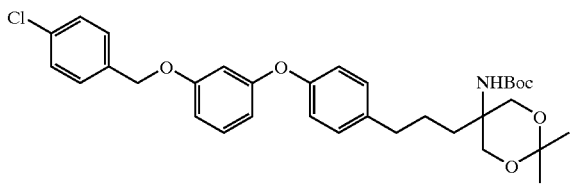

| Example | n | Yield (%) | Characteristics |
|---|---|---|---|
| 128 | 1 | 49 | Colorless oil |
| 129 | 3 | 67 | Colorless oil |

Example 130

5-t-butoxycarbonylamino-5-[4-(3-(4-chlorobenzyloxy)phenoxy)phenyl]propyl-2,2-dimethyl-1,3-dioxane Potassium carbonate (150 mg) and p-chlorobenzyl bromide (103 mg) were added to a DMF solution (5 mL) of the compound of Example 105 (150 mg) and the mixture was stirred for 1 hour at 70° C. Subsequently, the mixture was decanted into water and was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=3:1) to obtain the desired product (170 mg) as a colorless powder.

¹H-NMR (400 MHz, CDCl₃) δ 1.40(3H, s), 1.42(3H, s), 1.44(9H, s), 1.56–1.61(2H, m), 1.71(2H, br), 2.59(2H, t, J=7.3 Hz), 3.64(2H, d, J=11.7 Hz), 3.89(2H, d, J=11.7 Hz), 4.87(1H, br), 4.98(2H, s), 6.58–6.60(2H, m), 6.66–6.68(1H, m), 6.92(2H, d, J=8.3 Hz), 7.12(2H, d, J=8.3 Hz), 7.20 (1H, t, J=8.3 Hz), 7.34(4H, s)ₒ

Examples 131 through 143

The compounds of Example 105 and 106 were reacted with different alkylhalides in the same manner as in Example 130 described above to synthesize the compounds shown in Table 14 below:

TABLE 14

| Example | R | R' | Characteristics | Yield (%) |
|---|---|---|---|---|
| 131 | 3-Cl-C₆H₄-CH₂- | H | Colorless powder | 100 |
| 132 | 2-Cl-C₆H₄-CH₂- | H | Colorless powder | 100 |
| 133 | 3-Me-C₆H₄-CH₂- | Cl | Colorless powder | 75 |
| 134 | 3-MeO-C₆H₄-CH₂- | Cl | Colorless powder | 94 |
| 135 | 3-F₃C-C₆H₄-CH₂- | Cl | Colorless powder | 100 |
| 136 | 4-pyridyl-CH₂- | H | Colorless powder | 85 |
| 137 | 2-naphthyl-CH₂- | H | Colorless amorphous | 86 |
| 138 | PhCH=CH-CH₂- | H | Pale yellow powder | 100 |
| 139 | cyclohexyl-CH₂- | H | Colorless powder | 100 |
| 140 | PhCH₂- | H | Colorless amorphous | 76 |
| 141 | Ph₂CH | H | Colorless powder | 58 |

TABLE 14-continued

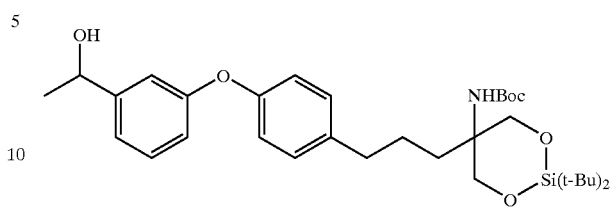

| Example | R | R' | Characteristics | Yield (%) |
|---|---|---|---|---|
| 142 | ![F3C-phenyl-CH2] | H | Colorless oil | 100 |
| 143 | ![Cl-phenyl-CH2] | Cl | Colorless powder | 84 |

Example 144

5-t-butoxycarbonylamino-2,2-di-t-butyl-5-[4-(3,5-bistrifluoromethylphenoxy)phenyloxy]ethyl-1,3,2-dioxasilane

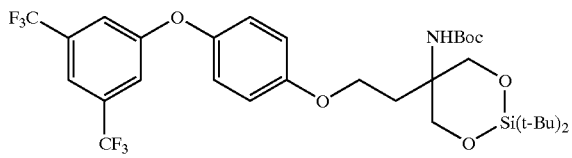

a) 5-t-butoxycarbonylamino-2,2-di-t-butyl-5-hydroxyethyl-1,3,2-dioxasilane

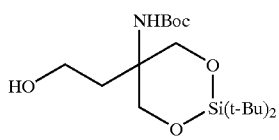

Using benzylbromoethylether and diethyl 2-t-butoxycarbonylaminomalonate, reactions were carried out in the same manner as in Example 1. Subsequently, the reaction processes of Examples 51 and 103 were sequentially followed to give the desired product as a colorless powder.

b) 5-t-butoxycarbonylamino-2,2-di-t-butyl-5-[4-(3,5-bistrifluoromethylphenoxy)phenyloxy]ethyl-1,3,2-dioxasilane Using the hydroxy derivative obtained above, reactions were carried out in the same manner as in Reference Example 164 to obtain an iodide, which in turn was reacted with 4-[(3,5-bistrifluoromethyl)phenoxy]phenol to give the desired product as a colorless amorphous.

$^1$H-NMR(400 MHz, CDCl$_3$) δ 1.08(9H, s), 1.11(9H, s), 1.44(9H, s), 2.04(2H, br s), 4.04–4.07(4H, br), 4.42(2H, d, J=11.2 Hz), 5.10(1H, br s), 6.92(2H, d, J=8.5 Hz), 7.00(2H, d, J=8.5 Hz), 7.32(2H, s), 7.52(1H, s)

Example 145

5-t-butoxycarbonylamino-2,2-di-t-butyl-5-[4-(3-(1-hydroxyethyl)phenoxy)phenyl]propyl-1,3,2-dioxasilane

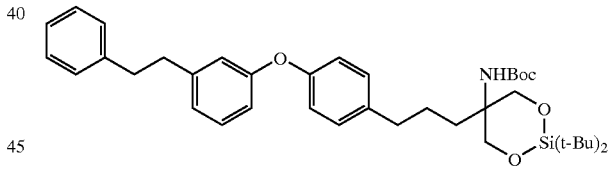

The compound of Example 125 (126 mg) was dissolved in THF (3.0 mL) and the solution was cooled to −78° C. under argon. A 1 mol/L methyllithium-ether solution (0.252 mL) was added to the solution and the temperature of the mixture was slowly raised to 0° C. A 5% aqueous solution of citric acid was added to the reaction mixture and the mixture was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=5:1) to obtain the desired product (90.7 mg) as a colorless oil.

$^1$H-NMR(400 MHz, CDCl$_3$) δ 1.05(9H, s), 1.07(9H, s), 1.42(9H, s), 1.48(3H, d, J=6.3 Hz), 1.55(4H, br s), 1.78(1H, m), 2.56(2H, t, J=6.8 Hz), 3.90(2H, d, J=11.7 Hz), 4.23(2H, d, J=11.7 Hz), 4.87(1H, q, J=6.5 Hz), 4.91(1H, br s), 6.86–6.89(1H, m), 6.92(2H, d, J=8.8 Hz), 7.03(1H, t, J=2.0 Hz), 7.07–7.12(3H, m), 7.29(1H, t, J=8.3 Hz)

Example 146

5-t-butoxycarbonylamino-2,2-di-t-butyl-5-[4-(3-phenetyl)phenoxy]phenyl]propyl-1,3,2-dioxasilane Benzylphosphonylchloride (152 mg) was dissolved in THF (2 mL) and sodium-t-butoxide (37.6 mg) was added to the solution at 0° C. The mixture was stirred for 30 minutes at room temperature and was again cooled to 0° C., at which time a THF solution (2 mL) of the compound of Example 125 (202 mg) was added. The reaction mixture was stirred for 1 hour at this temperature and for additional 1 hour at room temperature, followed by addition of a 5% aqueous solution of citric acid. The mixture was then extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=30:1) to give a styryl derivative as a colorless oil. The styryl derivative so obtained was reduced by catalytic reduction as in Reference Example 81 to obtain the desired product (168 mg) as a colorless oil.

$^1$H-NMR(400 MHz, CDCl$_3$) δ 1.05(9H, s), 1.07(9H, s), 1.43(9H, s), 1.57(4H, br s), 2.56(2H, t, J=7.1 Hz), 2.90(4H, m), 3.90(2H, d, J=11.2 Hz), 4.23(2H, d, J=11.2 Hz), 4.92 (1H, br s), 6.79–6.83(2H, m), 6.88(2H, d, J=8.3 Hz), 6.89–6.92(1H, m), 7.09(2H, d, J=8.3 Hz), 7.14–7.24(4H, m), 7.25–7.29(2H, m)

Example 147
2-amino-2-[4-(3,5-bistrifluoromethylphenoxy)phenyl]propyl-1,3-propanediol hydrochloride

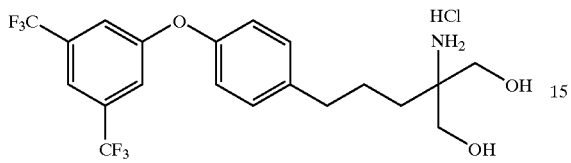

Ethyl acetate (20 mL) containing 3 mol/L hydrochloric acid was added to a methanol solution (10 mL) of the compound of Example 93 (1.28 g) and the mixture was stirred overnight at room temperature. The solvent was removed by distillation under reduced pressure. A mixture of ethyl acetate and hexane (ethyl acetate:hexane=1:1) was added to the residue and the crystals were collected by filtration. After drying, the desired product (1.07 g) was obtained as a colorless powder.

Alternatively, the compound of Example 124 was used in the reaction process of Example 150 to give the same product.

FABMS:438 ([M+H]+)

$^1$H-NMR (400 MHz, DMSO-d$_6$) δ 1.55–1.58(4H, br), 2.58(2H, t, J=6.8 Hz), 3.40–3.47(4H, m), 5.31(1H, br), 7.13(2H, d, J=8.3 Hz), 7.31(2H, d, J=8.3 Hz), 7.56(2H, s), 7.76(1H, br), 7.83(1H, s).

Melting point=194–196° C.

Elemental analysis (%): C$_{20}$H$_{21}$F$_6$NO$_3$·HCl

|  | C | H | N |
|---|---|---|---|
| Calcd. | 50.70 | 4.68 | 2.96 |
| Found | 50.70 | 4.66 | 2.91 |

Example 148
2-amino-2-[4-(3-phenylpropyloxyphenoxy)phenyl]propyl-1,3-propanediol hydrochloride

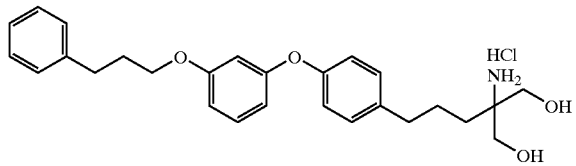

The compound of Example 138 was reduced by catalytic reduction as in Reference Example 81. Subsequently, the reaction processes of Example 147 were followed to give the desired product as a colorless powder.

Melting point: 95–98° C.

FABMS: 436 ([M+H]+)

$^1$H-NMR (400 MHz, DMSO-d$_6$) δ 1.56 (4H, br), 1.97(2H, quintet, 7.3 Hz), 2.49–2.53(2H, m), 3.39–3.46(4H, m), 3.92 (2H, t, J=7.3 Hz), 5.30(1H, br), 6.47–6.49(2H, m), 6.66–6.69 (1H, m), 6.95(2H, d, J=8.8 Hz), 7.12–7.29(8H, m), 7.68–7.72(2H, m)

Example 149
2-amino-2-[4'-(3,5-bistrifluoromethylphenoxy)cinnamyl]-1,3-propanediol hydrochloride

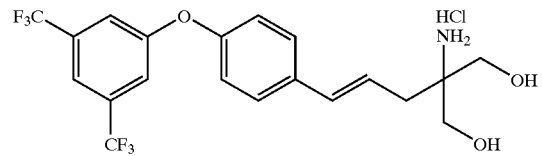

Using the compound of Example 100, reactions were carried out in the same manner as in Example 147 to obtain the desired product as a colorless powder.

Melting point=203–206° C.

FABMS: 436 ([M+H]+)

$^1$H-NMR (400 MHz, DMSO-d$_6$) δ 3.32(2H, d, J=7.5 Hz), 3.48(4H, br), 6.23(1H, dt, J=15.5, 7.5 Hz), 6.53(1H, d, 15.5 Hz), 7.17(2H, d, J=8.8 Hz), 7.52(2H, d, J=8.8 Hz), 7.60(2H, s), 7.85(1H, s)

Example 150
2-amino-2-[4-(3-isopropylphenoxy)phenyl]propyl-1,3-propanediol hydrochloride

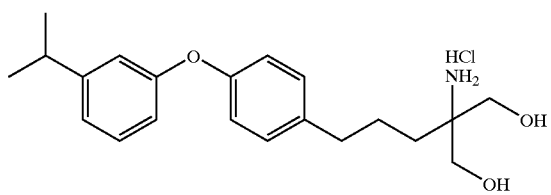

The compound of Example 109 (188 mg) was dissolved in THF (3.0 mL) and a 1 mol/L tetrabutylammonium-fluoride-THF solution (1.61 mL) was added to the solution. The mixture was stirred for 2 hours at room temperature. Subsequently, water was added to the mixture and the mixture was extracted with ethyl acetate. The organic phase was sequentially washed with water and a saturated aqueous solution of sodium chloride and was dried with anhydrous sodium sulfate. The solvent was then removed by distillation under reduced pressure. The residue was purified by silica gel column chromatography (hexane:ethyl acetate=3:2) to obtain the diol as a colorless oil. The diol so obtained was treated in the same manner as in Example 147 to give the desired product (107 mg) as a colorless amorphous.

FABMS: 344 ([M+H]+)

$^1$H-NMR (400 MHz, DMSO-d$_6$) δ 1.17(6H, d, J=6.8 Hz), 1.55(4H, br s), 2.53(2H, br), 2.81–2.89(1H, m), 3.39–3.49 (4H, m), 5.30(2H, t, J=5.1 Hz), 6.71(1H, dd, J=8.3, 2.4 Hz), 6.87(1H, t, J=2.0 Hz), 6.91(2H, d, J=8.8 Hz), 6.99(1H, d, J=8.3 Hz), 7.19(2H, d, J=8.8 Hz), 7.26(1H, t, J=8.3 Hz), 7.71(3H, br s)

Examples 151 through 166

The compounds of Examples 110 through 123 and the compounds of Examples 145 and 146 were treated in the same manner as in Example 150 above to synthesize the compounds shown in Table 15 below:

TABLE 15

| Example | R1 | R2 | Yield (%) | Characteristics | FABMS [M + H]+ | Melting Point (° C.) |
|---|---|---|---|---|---|---|
| 151 | F | H | 88 | Colorless powder | 320 | 131–133 |
| 152 | Cl | H | 88 | Colorless powder | 336 | 125–127 |
| 153 | Br | H | 88 | Colorless powder | 380 | 154–156 |
| 154 | Me | H | 92 | Pale brown amorphous | 316 | |
| 155 | Ph | H | 87 | Colorless powder | 378 | 164–166 |
| 156 | MeO | H | 83 | Pale brown amorphous | 332 | |
| 157 | EtO | H | 88 | Colorless powder | 346 | 115–117 |
| 158 | CF$_3$O | H | 86 | Pale brown amorphous | 386 | |
| 159 | CH$_2$OH | H | 84 | Colorless powder | 332 | 180–182 |
| 160 | Ac | H | 85 | Yellow amorphous | 344 | |
| 161 | NO$_2$ | H | (9) | Pale yellow amorphous | 347 | |
| 162 | CN | H | 92 | Pale yellow oil* | 327 | |
| 163 | F | F | 79 | Pale yellow amorphous | 338 | |
| 164 | Cl | Cl | 82 | Pale yellow powder** | 370 | 75–77 |
| 165 | Ph(CH$_2$)$_2$ | H | 85 | Colorless powder | 406 | 165–167 |
| 166 | MeCH(OH) | H | 85 | Yellow amorphous | 346 | |

In the parentheses( ), shown is the total yield from the previous table.
The mark "*" means it was isolated as a CF$_3$CO$_2$H salt.
The mark "**" means it was isolated as free form.

Example 167

2-amino-2-[4-(3,5-bistrifluoromethylphenoxy)phenoxy]ethyl-1,3-propanediol hydrochloride

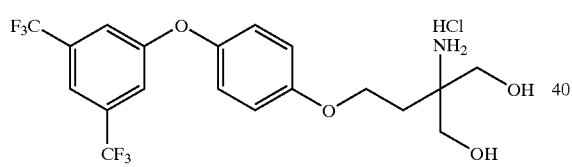

Using the compound of Example 144, reactions were carried out in the same manner as in Example 150 to obtain the desired product as a colorless powder.

Melting point=151–155° C.

FABMS: 440 ([M+H]+)

$^1$H-NMR (400 MHz, DMSO-d$_6$) δ 2.04(2H, t, J=6.5 Hz), 3.54(4H, s), 4.11(2H, d,J=6.5 Hz), 7.04(2H, d, J=9.2 Hz), 7.19(2H, d, J=9.2 Hz), 7.50(2H, s), 7.80(1H, s)

Examples 168 through 171

The compounds of Examples 96 and 126 through 129 were treated in the same manner as in Example 150 above to synthesize the compounds shown in Table 16 below:

TABLE 16

| Example | R1 | R2 | n | Yield (%) | Characteristics | FABMS [M + H]+ | Melting point (° C.) |
|---|---|---|---|---|---|---|---|
| 168 | Cl | Cl | 0 | 80 | Colorless powder | 342 | 110–111 |
| 169 | Cl | Cl | 1 | 99 | Pale yellow amorphous | 356 | |
| 170 | Cl | Cl | 3 | 89 | Colorless amorphous | 384 | |
| 171 | CF$_3$ | CF$_3$ | 1 | 81 | Colorless powder | 424 | 116–118 |
| 172 | CF$_3$ | CF$_3$ | 3 | 96 | Colorless amorphous | 452 | |

Example 173
2-amino-2-[4-(3-benzyloxyphenoxy)-2-chlorophenyl]propyl-1,3-propanediol hydrochloride

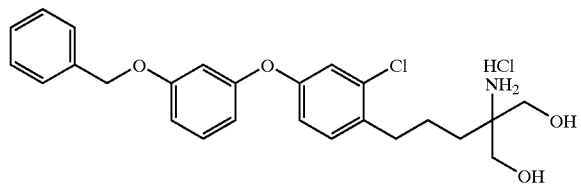

The compound of Example 51 was treated in the same manner as in Example 147 to obtain the desired product as a colorless powder.

FABMS: 442 ([M+H]+)

$^1$H-NMR (400 MHz, DMSO-d$_6$) δ 1.58(4H, br s), 2.63 (2H, br s), 3.39–3.45(4H, m), 5.08(2H, s), 5.31(2H, br), 6.56(1H, dd, J=8.3, 2.4 Hz), 6.66(1H, t, J=2.4 Hz), 6.83(1H, dd, J=8.3, 2.4 Hz), 6.94(1H, dd, J=8.3, 2.4 Hz), 7.05(1H, d, J=2.4 Hz), 7.28–7.43(7H, m), 7.71(3H, br)

Melting point=105–106° C. (EtOH-iPr20)

Elemental analysis(%): $C_{25}H_{28}ClNO_4 \cdot HCl$

|  | C | H | N |
|---|---|---|---|
| Calcd. | 62.76 | 6.11 | 2.93 |
| Found | 62.76 | 6.05 | 2.92 |

Examples 174 through 233

The compounds of Examples 52 through 91, 94, 95, 107, 108, and 130 through 143 were treated in the same manner as in Example 147 to synthesize the compounds shown in Tables 17 and 18 below:

TABLE 17

| Example | R1 | R2 | R3 | R4 | Yield (%) | Characteristics | FABMS [M + H]$^+$ | Melting point (° C.) |
|---|---|---|---|---|---|---|---|---|
| 174 | CF$_3$ | H | H | H | 89 | Colorless powder | 370 | 146–148 |
| 175 | CF$_3$ | H | MeO | H | 100 | Colorless oil | 400 | |
| 176 | CF$_3$ | H | H | MeO | 92 | Colorless amorphous | 400 | |
| 177 | CF$_3$ | H | Cl | H | 100 | Colorless powder | 404 | 120–122 |
| 178 | CF$_3$ | H | H | Cl | 100 | Colorless amorphous | 404 | |
| 179 | CF$_3$ | H | H | PhCH$_2$O | 85 | Colorless powder | 476 | 120–123 |
| 180 | CF$_3$ | H | CF$_3$ | H | 99 | Colorless powder | 438 | 124–128 |
| 181 | CF$_3$ | H | H | CF$_3$ | 90 | Colorless amorphous | 438 | |
| 182 | CF$_3$ | CF$_3$ | H | Cl | 79 | Colorless powder | 472 | 123–125 |
| 183 | CF$_3$ | Ph(CH$_2$)$_2$ | H | H | 87 | Colorless powder | 474 | 110–112 |
| 184 | CF$_3$ | H | H | F | 85 | Colorless oil | 388 | |
| 185 | Ph(CH$_2$)$_2$ | Ph(CH$_2$)$_2$ | H | H | 96 | Colorless amorphous | 510 | |
| 186 | Ph(CH$_2$)$_2$ | H | H | Cl | 91 | Colorless amorphous | 440 | |
| 187 | Ph(CH$_2$)$_2$ | H | H | CF$_3$ | 94 | Colorless amorphous | 474 | |
| 188 | Ph(CH$_2$)$_2$ | Ph(CH$_2$)$_2$ | H | Cl | 93 | Colorless amorphous | 544 | |
| 189 | Ph(CH$_2$)$_2$ | Ph(CH$_2$)$_2$ | H | CF$_3$ | 93 | Colorless amorphous | 578 | |
| 190 | PhCH$_2$O | H | H | H | 91 | Colorless amorphous | 408 | |
| 191 | PhCH$_2$O | PhCH$_2$O | H | H | 100 | Colorless powder | 514 | 92–95 |
| 192 | PhCH$_2$O | PhCH$_2$O | H | Cl | 100 | Colorless amorphous | 548 | |
| 193 | PhCH$_2$O | Cl | H | Cl | 91 | Colorless powder | 476 | 89–91 |
| 194 | PhCH$_2$O | H | H | Br | 98 | Colorless amorphous | 488 | |
| 195 | PhCH$_2$O | H | H | CF$_3$ | 100 | Colorless powder | 476 | 72–76 |
| 196 | PhCH$_2$O | H | H | Ph | 98 | Colorless amorphous | 484 | |
| 197 | PhCH$_2$O | CF$_3$ | H | H | 91 | Colorless amorphous | 476 | |
| 198 | PhCH$_2$O | CF$_3$ | H | Cl | 94 | Colorless powder | 510 | 114–118 |
| 199 | t-Bu | H | H | H | 100 | Colorless amorphous | 358 | |
| 200 | MeS | H | H | H | 89 | Colorless amorphous | 348 | |
| 201 | n-C$_5$H$_{11}$ | H | H | H | 99 | Colorless amorphous | 372 | |
| 202 | n-C$_7$H$_{15}$ | H | H | H | 74 | Yellow amorphous | 400 | |
| 203 | i-Pr | iPrO | H | H | 93 | Colorless amorphous | 402 | |
| 204 | i-Pr | iPrO | H | Cl | 97 | Colorless amorphous | 436 | |
| 205 | i-Pr | i-Pr | H | Cl | 95 | Colorless amorphous | 420 | |
| 206 | Cl | Cl | H | Cl | 92 | Colorless amorphous | 404 | |
| 207 | PhCH$_2$S | H | H | H | 100 | Colorless amorphous | 424 | |
| 208 | PhCH$_2$S | H | H | Cl | 100 | Colorless amorphous | 458 | |
| 209 | Et | H | H | H | 87 | Pale yellow amorphous | 330 | |
| 210 | i-Bu | H | H | H | 92 | Colorless amorphous | 358 | |
| 211* | OH | H | H | H | 98 | Colorless powder | 318 | 174–176 |
| 212 | i-PrO | H | H | H | 94 | Colorless amorphous | 360 | |
| 213 | PhO | H | H | H | 100 | Colorless amorphous | 394 | |

The mark "*" means the step was carried out after catalytic reduction of the compound of Example 68.

TABLE 18

| Example | R1 | R2 | R3 | R4 | Yield (%) | Characteristics | FABMS [M + H]+ | Melting point ° C. |
|---|---|---|---|---|---|---|---|---|
| 214 | 3-(CF₃)C₆H₄CH₂O | H | H | H | 100 | Colorless powder | 476 | 89–92 |
| 215 | 4-pyridyl-CH₂O | H | H | H | 85 | Colorless amorphous | 409 | |
| 216 | 2-naphthyl-CH₂O | H | H | H | 93 | Colorless powder | 458 | 170–173 |
| 217 | Ph₂CHO | H | H | H | 91 | Colorless powder | 484 | 153–156 |
| 218 | Ph(CH₂)₂O | H | H | H | 90 | Colorless amorphous | 422 | |
| 219 | PhCH=CHCH₂O | H | H | H | 100 | Colorless amorphous | 434 | |
| 220 | PhOCH₂ | H | H | H | 97 | Colorless powder | 408 | 119–122 |
| 221 | MeSO | H | H | H | 100 | Colorless amorphous | 364 | |
| 222 | MeSO₂ | H | H | H | 100 | Colorless powder | 380 | 147–150 |
| 223** | CF₃ | H | H | OH | 97 | Colorless amorphous | 386 | |
| 224 | 3-Cl-C₆H₄CH₂O | H | H | Cl | 100 | Colorless powder | 476 | 94–96 |
| 225 | 3,5-Cl₂-C₆H₃CH₂O | H | H | Cl | 83 | Colorless powder | 510 | 92–95 |
| 226 | 3-MeO-C₆H₄CH₂O | H | H | Cl | 94 | Colorless amorphous | 472 | |
| 227 | 3-Me-C₆H₄CH₂O | H | H | Cl | 100 | Colorless powder | 456 | 84–86 |
| 228 | 3-(CF₃)C₆H₄CH₂O | H | H | Cl | 76 | Colorless powder | 510 | 88–91 |
| 229 | PhCH₂O | H | H | i-Pr | 97 | Colorless amorphous | 450 | |
| 230 | cyclohexyl-CH₂O | H | H | H | 90 | Colorless powder | 414 | 125–127 |

TABLE 18-continued

| Example | R1 | R2 | R3 | R4 | Yield (%) | Characteristics | FABMS [M + H]+ | Melting point ° C. |
|---|---|---|---|---|---|---|---|---|
| 231 | 4-Cl-C6H4-CH2O | H | H | H | 100 | Colorless powder | 442 | 195–197 |
| 232 | 3-Cl-C6H4-CH2O | H | H | H | 100 | Colorless powder | 442 | 130–132 |
| 233 | 2-Cl-C6H4-CH2O | H | H | H | 100 | Colorless powder | 442 | 94–96 |

The mark "**" means the step was carried out after catalytic reduction of the compound of Example 57.

Examples 234 through 243

Using the compounds of Reference Examples 241 through 250, reactions were carried out in the same manner as in Example 1 to synthesize the compounds below:

TABLE 19

| Example | R1 | R2 | R3 | R4 | Characteristics | Yield (%) |
|---|---|---|---|---|---|---|
| 234 | Ph(CH2)2 | c-CF3 | H | Cl | Colorless oil | 93 |
| 235 | PhCH2O | c-H | H | Me | Colorless oil | 100 |
| 236 | PhCH2O | c-H | H | Et | Colorless oil | 72 |
| 237 | PhCH2O | c-H | H | SMe | Colorless oil | — |
| 238 | PhO | c-H | H | Cl | Colorless oil | 92 |
| 239 | CF3 | a-Cl | H | H | Colorless oil | 100 |
| 240 | CF3 | b-Cl | H | H | Colorless oil | 94 |
| 241 | CF3 | d-Cl | H | H | Pale yellow oil | 72 |
| 242 | CF3 | c-Cl | H | H | Pale yellow oil | 41 |
| 243 | PhCH2O | c-H | H | F | Colorless oil | — |

The mark "—" means yield is shown in Table 20 as a total yield.

Example 244

Ethyl 4-[4-(3-benzyloxyphenoxy)-2-chloro]phenyl-2-t-butoxycarbonylamino-2-ethoxycarbonylbutyrate

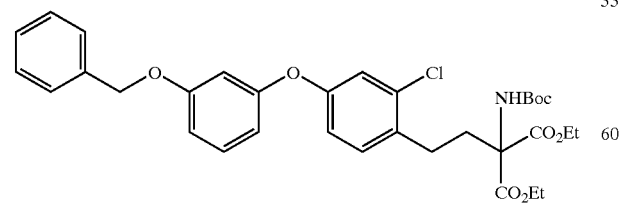

Using the compound of Example 261, reactions were carried out in the same manner as in Example 1 to obtain the desired product as a colorless oil.

$^1$H-NMR(400 MHz, CDCl$_3$) δ 1.23–1.32(6H, m), 1.45 (9H, s), 2.59(4H, br), 4.22–4.34(4H, m), 5.03(2H, s), 6.58–6.62(2H, m), 6.75(1H, dd, J=8.3 Hz, 2.4 Hz), 6.83(1H, dd, J=8.3 Hz, 2.4 Hz), 6.98(1H, d, J=2.4 Hz), 7.12(1H, d, J=8.3 Hz), 7.23(1H, t, J=8.3 Hz), 7.30–7.42(5H, m)

Example 245

Ethyl 6-[4-(3-benzyloxyphenoxy)-2-chloro]phenyl-2-t-butoxycarbonylamino-2-ethoxycarbonylhexanoate Using the compound of Example 262, reactions were carried out in the same manner as in Example 1 to obtain the desired product as a colorless oil.

$^1$H-NMR (400 MHz, CDCl$_3$) δ 1.24(6H, t, J=7.3 Hz), 1.43(9H, s), 1.58–1.67(4H, m), 2.33(2H, br), 2.67(2H, t, J=7.8 Hz), 4.18–4.32(4H, m), 5.03(2H, s),5.95(1H, br s), 6.57–6.60(1H, m), 6.62(1H, t, J=2.4 Hz), 6.74(1H, dd, J=8.3 Hz, 2.4 Hz), 6.83(1H, dd, J=8.3 Hz, 2.4 Hz), 6.99(1H, d, J=2.4 Hz), 7.12(1H, d, J=8.3 Hz), 7.23(1H, t, J=8.3 Hz), 7.30–7.42(5H, m)

Examples 246 through 255

Using the compounds of Examples 234 through 243, reactions were carried out in the same manner as in Example 51 to synthesize the compounds below:

TABLE 20

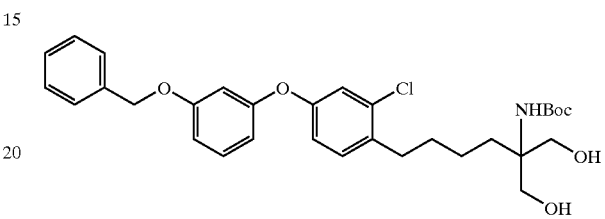

| Reference example | R1 | R2 | R3 | R4 | Characteristics | Yield (%) |
|---|---|---|---|---|---|---|
| 246 | Ph(CH$_2$)$_2$ | c-CF$_3$ | H | Cl | Colorless oil | 46 |
| 247 | PhCH$_2$O | c-H | H | Me | Colorless oil | 75 |
| 248 | PhCH$_2$O | c-H | H | Et | Colorless oil | 61 |
| 249 | PhCH$_2$O | c-H | H | SMe | Colorless oil | 38 |
| 250 | PhO | c-H | H | Cl | Colorless oil | 76 |
| 251 | CF$_3$ | a-Cl | H | H | Colorless oil | 57 |
| 252 | CF$_3$ | b-Cl | H | H | Colorless oil | 62 |
| 253 | CF$_3$ | d-Cl | H | H | Colorless oil | 37 |
| 254 | CF$_3$ | c-Cl | H | H | Colorless oil | 51 |
| 255 | PhCH$_2$O | c-H | H | F | Colorless oil | 34 |

Example 256

2-[4-(3-benzyloxyphenoxy)-2-chlorophenyl]ethyl-2-t-butoxycarbonylamino-1,3-propanediol

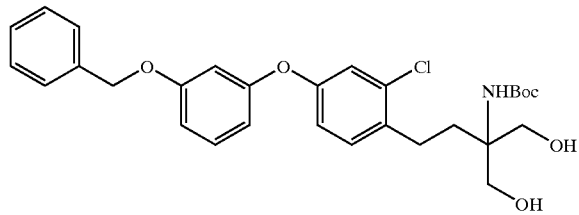

The compound of Example 244 was treated in the same manner as in Example 51 to obtain the desired product as a colorless powder.

$^1$H-NMR (400 MHz, CDCl$_3$) δ 1.46(9H, s), 1.83–1.87 (2H, m), 2.69–273(2H, m), 3.35(2H, br), 3.67(2H, dd, J=11.7 Hz, 5.9 Hz), 3.92(2H, dd, J=11.7 Hz, 4.9 Hz), 5.03(2H, s), 5.10(1H, s), 6.57–6.62(2H, m), 6.75(1H, dd, J=8.3 Hz, 2.4 Hz), 6.85(1H, dd, J=8.3 Hz, 2.4 Hz), 7.00(1H, d, J=2.4 Hz), 7.17(1H, d, J=8.3 Hz), 7.24(1H, t, J=8.3 Hz), 7.32–7.42(5H, m)

Example 257

2-[4-(3-benzyloxyphenoxy)-2-chlorophenyl]butyl-2-t-butoxycarbonylamino-1,3-propanediol The compound of Example 245 was treated in the same manner as in Example 51 to obtain the desired product as a colorless oil.

$^1$H-NMR (400 MHz, CDCl$_3$) δ 1.44(9H, s), 1.61(6H, br), 2.70(2H, t, J=7.3 Hz), 3.46(2H, br), 3.57–3.60(2H, m), 3.84(2H, d, J=9.8 Hz), 4.92(1H, s), 5.03(2H, s), 6.59–6.63 (2H, m), 6.73–6.76(1H, m), 6.84(1H, dd, J=8.3 Hz, 2.4 Hz), 7.00(1H, d, J=2.4 Hz), 7.13(1H, d, J=8.3 Hz), 7.24(1H, t, J=8.3 Hz), 7.23–7.43(5H, m)

Examples 258 through 267

Using the compounds of Examples 246 through 255, reactions were carried out in the same manner as in Example 147 to synthesize the compounds below:

TABLE 21

| Example | R1 | R2 | R3 | R4 | Yield (%) | Characteristics | FABMS [M + H]$^+$ | Melting point (° C.) |
|---|---|---|---|---|---|---|---|---|
| 258 | Ph(CH$_2$)$_2$ | c-CF$_3$ | H | Cl | 96 | Pale yellow amorphous | 508 | |
| 259 | PhCH$_2$O | c-H | H | Me | 92 | Yellow amorphous | 422 | |
| 260 | PhCH$_2$O | c-H | H | Et | 100 | Pale yellow amorphous | 436 | |
| 261 | PhCH$_2$O | c-H | H | SMe | 100 | Colorless amorphous | 454 | |
| 262 | PhO | c-H | H | Cl | 92 | Colorless amorphous | 428 | |
| 263 | CF$_3$ | a-Cl | H | H | 93 | Pale yellow amorphous | 404 | |
| 264 | CF$_3$ | b-Cl | H | H | 99 | Colorless powder | 404 | 133–136 |
| 265 | CF$_3$ | d-Cl | H | H | 78 | Pale yellow amorphous | 404 | |
| 266 | CF$_3$ | c-Cl | H | H | 76 | Colorless powder | 404 | 180–182 |
| 267 | PhCH$_2$O | c-H | H | F | 100 | Colorless powder | 426 | 71–73 |

Example 268
2-amino-2-[4-(3-benzyloxyphenoxy)-2-chlorophenyl]ethyl-1,3-propanediol hydrochloride

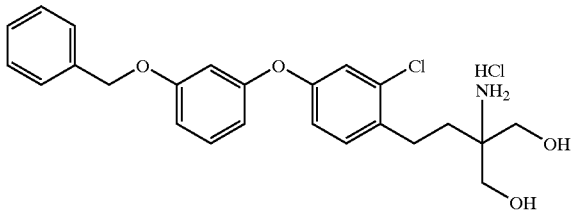

The compound of Example 256 was treated in the same manner as in Example 147 to obtain the desired product as a colorless powder.

FABMS: 428 ([M+H]+)

$^1$H-NMR(400 MHz, DMSO-$d_6$) δ 1.75–1.79(2H, m), 2.68–2.72(2H, m), 3.51–3.55(4H, m), 5.08(2H, s), 5.40(2H, t, J=4.9 Hz), 6.57(1H, dd, J=8.3 Hz, 2.4 Hz), 6.67(1H, t, J=2.4 Hz), 6.83(1H, dd, J=8.3 Hz, 2.4 Hz), 6.95(1H, dd, J=8.3 Hz, 2.4 Hz), 7.05(1H, d, J=2.4 Hz), 7.27–7.43(7H, m), 7.88(3H, br)

Melting point=150–152° C.

Example 269
2-amino-2-[4-(3-benzyloxyphenoxy)-2-chlorophenyl]butyl-1,3-propanediol hydrochloride

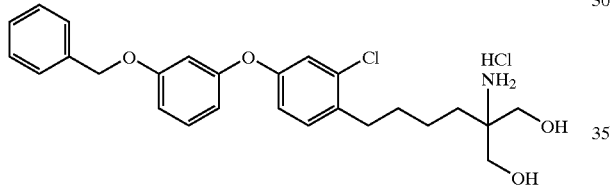

The compound of Example 257 was treated in the same manner as in Example 147 to obtain the desired product as a pale yellow amorphous.

FABMS: 456 ([M+H]+)

$^1$H-NMR(400 MHz, DMSO-$d_6$) δ 1.30–1.40(2H, m), 1.46–1.60(4H, m), 2.64(2H, t, J=7.8 Hz), 3.39–3.48(4H, m), 5.08(2H, s), 5.32(2H, t, J=5.4 Hz), 6.57(1H, dd, J=8.3 Hz, 2.4 Hz), 6.67(1H, t, J=2.4 Hz), 6.82(1H, dd, J=8.3 Hz, 2.4 Hz), 6.91(1H, dd, J=8.3 Hz, 2.4 Hz), 7.03(1H, d, J=2.4 Hz), 7.27–7.43(7H, m), 7.76(3H, br)

Melting point=95–97° C.

The following experiments were conducted to prove the effectiveness of the compounds of the present invention.

<Experiment 1>

Ability of Test Compounds to Suppress Host vs Graft Rejection in Mice

This experiment was performed according to the method described in *Transplantation*, 55, No.3 (1993): 578–591. Spleens were collected from 9 to 11 week old male BALB/c mice (CLEA JAPAN Inc., CHARLES RIVER JAPAN Inc., or JAPAN SLC Inc.). The spleens were placed in a phosphate-buffered saline (PBS(-), NISSUI PHARMACEUTICAL Co., Ltd.) or in an RPMI-1640 medium (GIBCO INDUSTRIES Inc., or IWAKI GLASS Co., Ltd.) and were either passed through a stainless steel mesh, or gently pressed between two slide glasses and then passed through a cell strainer (70 μm, Falcon), to form a cell suspension. The suspension was then centrifuged and the supernatant was discarded. An ammonium chloride-Tris isotonic buffer was added to the suspension to lyse erythrocytes. The cells were then centrifuged and washed three times in PBS (-) or RPMI-1640 medium and were resuspended in an RPMI-1640 medium. To this suspension, mitomycin C (KYOWA HAKKO KOGYO Co., Ltd.) was added to a final concentration of 25 μg/mL and the suspension was incubated for 30 minutes at 37° C. in a 5% $CO_2$ atmosphere. The cells were again centrifuged and washed in PBS (-) or RPMI-1640 medium and were resuspended in an RPMI-1640 medium so that the medium would contain $2.5 \times 10^8$ cells/mL. This suspension served as a "stimulation cell suspension." Using a 27G needle along with a microsyringe (Hamilton), 20 μL ($5 \times 10^6$ cells/mouse) of the stimulation cell suspension was subcutaneously injected into the right hind footpad of 7 to 9 week old male C3H/HeN mice (CLEA JAPAN Inc., CHARLES RIVER JAPAN Inc., or JAPAN SLC Inc.). A group of mice was injected with RPMI-1640 medium alone to serve as normal control. 4 days after the injection, right popliteal lymph nodes were collected and were weighed on a Mettler AT201 electronic scale (METTLER TOLEDO Co., Ltd.). Each animal was intraperitoneally administered a test compound once a day for four consecutive days starting on the day of the injection of the stimulation cells (i.e., total of 4 times). Controls were administered a vehicle that has the same composition as that used in the preparation of the test compounds. The results are shown in Table 22 below:

TABLE 22

| Example No. | Dose (mg/kg) | Inhibition (%) |
|---|---|---|
| 147 | 10 | 82 |
| 148 | 3 | 78 |
| 150 | 10 | 78 |
| 157 | 10 | 50 |
| 164 | 10 | 82 |
| 166 | 10 | 91 |
| 169 | 10 | 86 |
| 170 | 10 | 71 |
| 171 | 10 | 79 |
| 172 | 10 | 78 |
| 173 | 3 | 100 |
| 174 | 10 | 62 |
| 175 | 10 | 64 |
| 176 | 10 | 63 |
| 177 | 10 | 71 |
| 178 | 10 | 82 |
| 181 | 10 | 96 |
| 182 | 3 | 78 |
| 183 | 3 | 102 |
| 184 | 3 | 64 |
| 185 | 3 | 63 |
| 186 | 1 | 87 |
| 187 | 3 | 76 |
| 188 | 3 | 68 |
| 189 | 3 | 54 |
| 190 | 10 | 83 |
| 191 | 3 | 95 |
| 192 | 0.3 | 93 |
| 194 | 0.3 | 85 |
| 195 | 3 | 69 |
| 197 | 3 | 93 |
| 198 | 3 | 92 |
| 200 | 10 | 50 |
| 202 | 10 | 92 |
| 203 | 10 | 77 |
| 204 | 10 | 79 |
| 205 | 10 | 84 |
| 206 | 10 | 76 |
| 207 | 3 | 69 |
| 208 | 3 | 90 |
| 209 | 10 | 71 |
| 210 | 10 | 76 |

TABLE 22-continued

| Example No. | Dose (mg/kg) | Inhibition (%) |
|---|---|---|
| 212 | 10 | 78 |
| 213 | 3 | 68 |
| 214 | 3 | 79 |
| 215 | 3 | 76 |
| 217 | 3 | 66 |
| 218 | 3 | 92 |
| 219 | 3 | 53 |
| 220 | 3 | 77 |
| 223 | 10 | 63 |
| 224 | 0.3 | 76 |
| 225 | 0.03 | 70 |
| 226 | 3 | 89 |
| 227 | 3 | 93 |
| 228 | 0.3 | 74 |
| 230 | 3 | 67 |
| 231 | 3 | 83 |
| 232 | 3 | 92 |
| 233 | 3 | 85 |

<Experiment 2>
Ability of Test Compounds to Suppress Delayed-type Hypersensitivity in Mice.

This experiment was performed according to the method described in *Methods in Enzymology*, 300 (1999): 345–363. 1-fluoro-2,4-dinitrobenzene (DNFB, NACALAI TESQUE Inc.) was dissolved in a mixture of acetone and olive oil (acetone:olive oil=4:1) to a concentration of 1% (v/v). 10 μL of this 1% DNFB solution was applied to the footpad of each hind leg of male BALB/c mice (JAPAN SLC Inc. or CHARLES RIVER JAPAN Inc.) for sensitization. The sensitization was done for 2 consecutive days (day 0 and day 1). On day 5, the ears of the mice were challenged with the antigen to induce delayed-type hypersensitive responses: First, the thickness of each ear was measured by the dial thickness gauge G (0.01–10 mm, OZAKI MFG Co., Ltd.). Next, a test compound was administered. 30 minutes after the administration, 10 μL of a 0.2% (v/v) DNFB solution was applied to the inner and outer surfaces of the right ear of each animal for antigen challenge. The left ear of each animal was challenged with the solvent alone. 24 hours after the challenge, the increase in the ear thickness was measured for each ear and the difference between the right and the left ears was determined for each individual. The test compound was dissolved, or suspended, in an ultra pure water and was orally administered at a dose of 0.1 mL/10 g of body weight. A control group was administered ultra pure water alone. The results are shown in Table 23 below:

TABLE 23

| Example No. | Dose (mg/kg) | Inhibition (%) |
|---|---|---|
| 173 | 3 | 64 |
| 178 | 10 | 72 |
| 181 | 10 | 69 |
| 182 | 30 | 101 |
| 190 | 3 | 67 |
| 195 | 30 | 64 |
| 198 | 3 | 57 |

<Experiment 3>
Activities of Test Compounds on Skin Transplantation Model in Mice Effects of the test compounds were examined on skin transplantation model in mice. The experimental procedure was referred to the method described in *Journal of Experimental Biology*, 28, No.3 (1951); 385–405.

First, dorsal skin from male DBA/2 mice were stripped of the fatty layer and the panniculus carnosus, and cut into circular grafts with a diameter of 8 mm. Next, graft bed, a circular area, approximately 8 mm in diameter, was prepared in the back of anesthetized male BALB/c mice with a scalpel while the skin was pinched by forceps. Each graft obtained from the DBA/2 mice was placed on the graft bed formed in the backs of the BALB/c mice and was secured with a strip of adhesive bandage while held down from the top. 6 days after transplantation, the bandage was removed and the graft was subsequently observed everyday. The activity of each compound was evaluated based on the length of the survival period, which is defined as the number of days for rejection. Each test compound was dissolved in ultra pure water and was orally administered once a day, starting from the day of transplantation. In a similar manner, the control group was administered ultra pure water alone.

Figure 2:
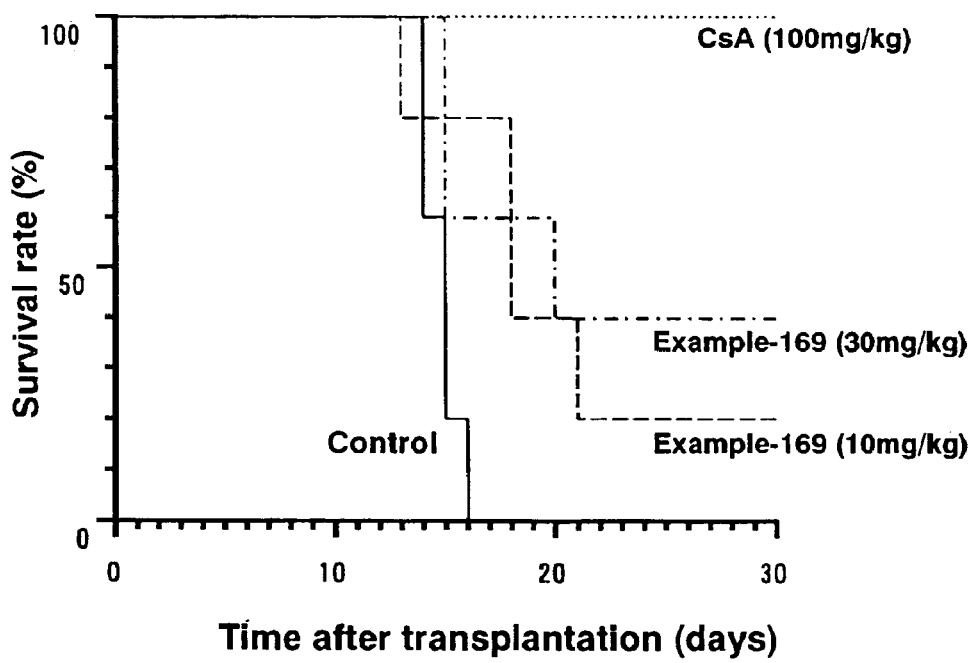
FIG. 2 is a graph showing activities of a test compound in a mouse skin graft model.
Figure 3:
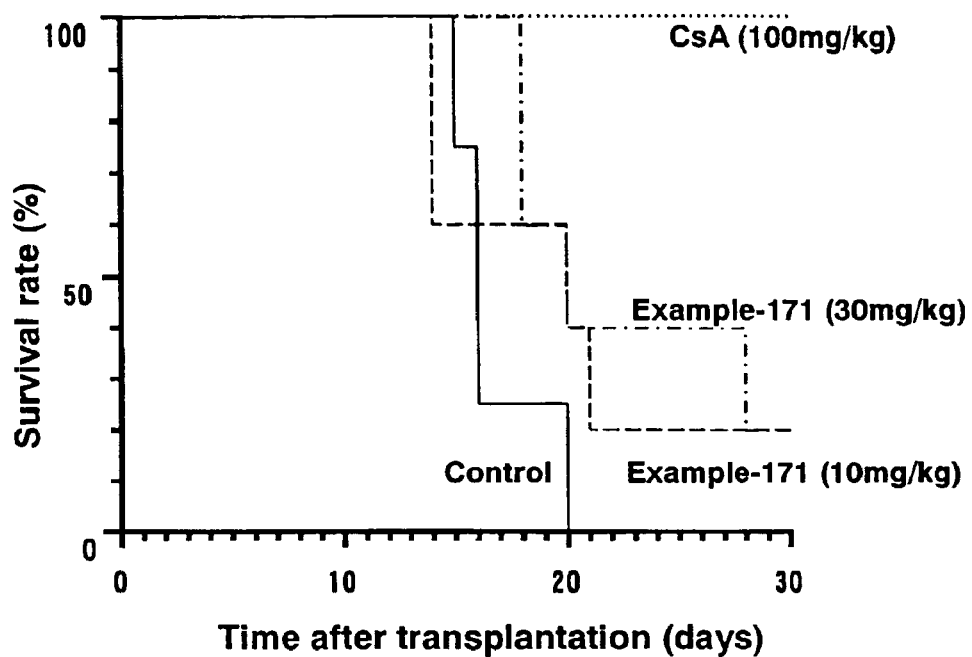
FIG. 3 is a graph showing activities of a test compound in a mouse skin graft model.
Figure 4:
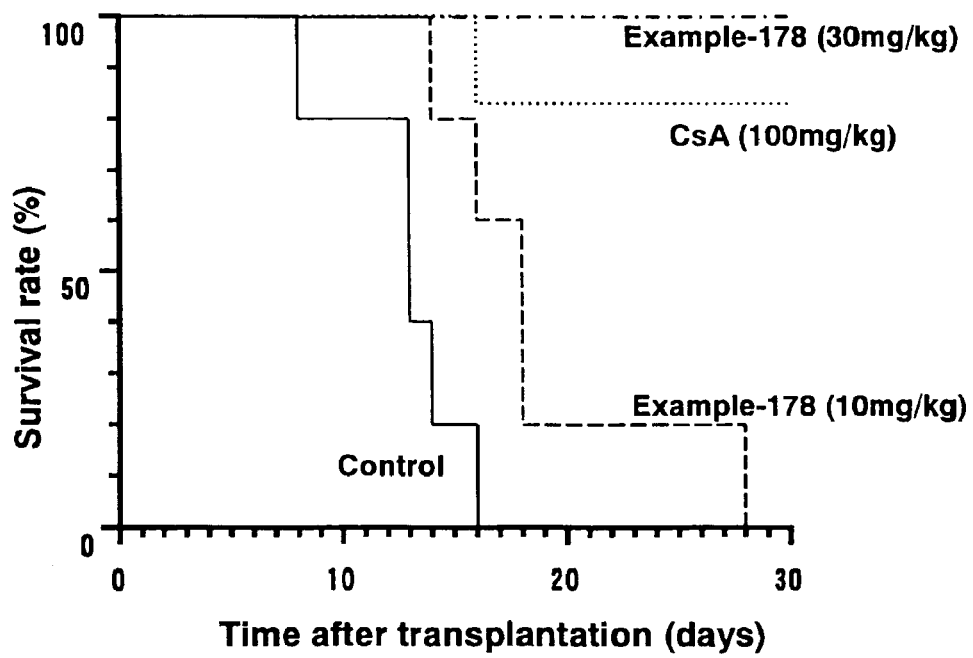
FIG. 4 is a graph showing activities of a test compound in a mouse skin graft model.
Figure 5:
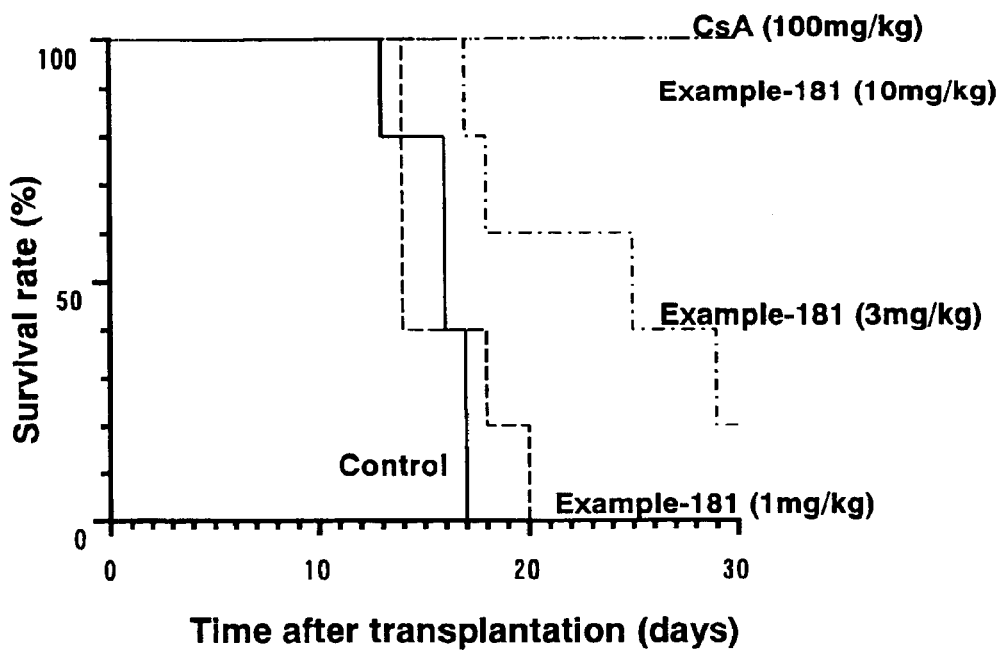
FIG. 5 is a graph showing activities of a test compound in a mouse skin graft model.
Figure 6:
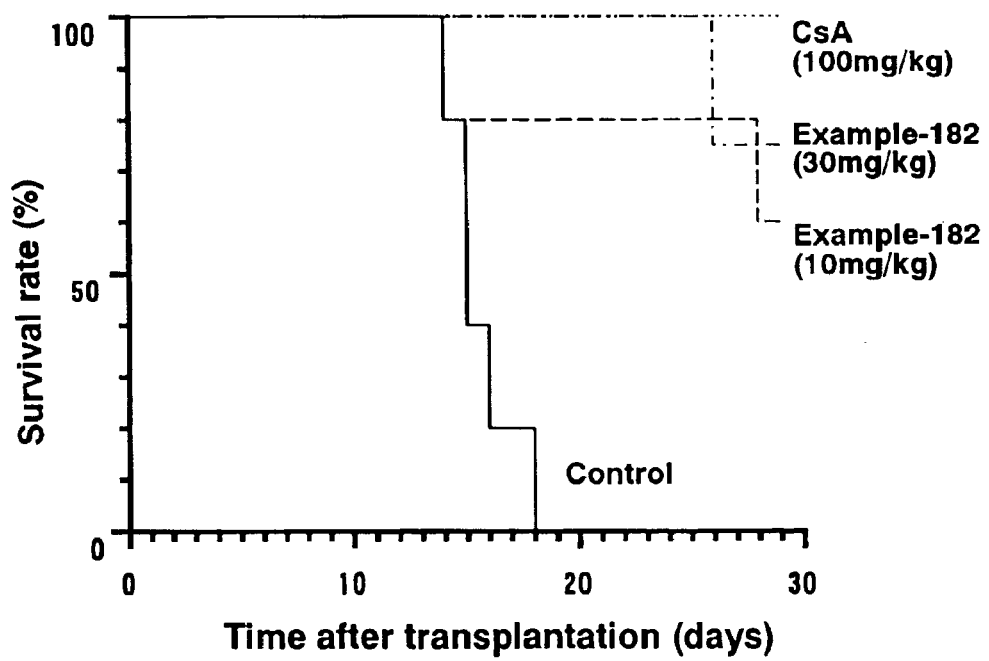
FIG. 6 is a graph showing activities of a test compound in a mouse skin graft model.
Figure 7:
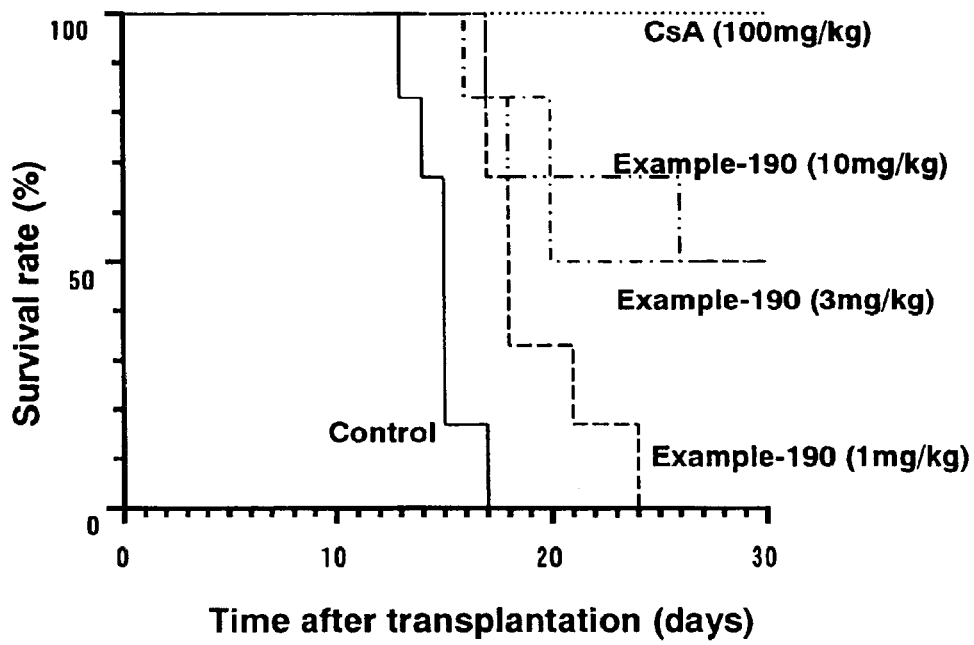
FIG. 7 is a graph showing activities of a test compound in a mouse skin graft model.
Figure 8:
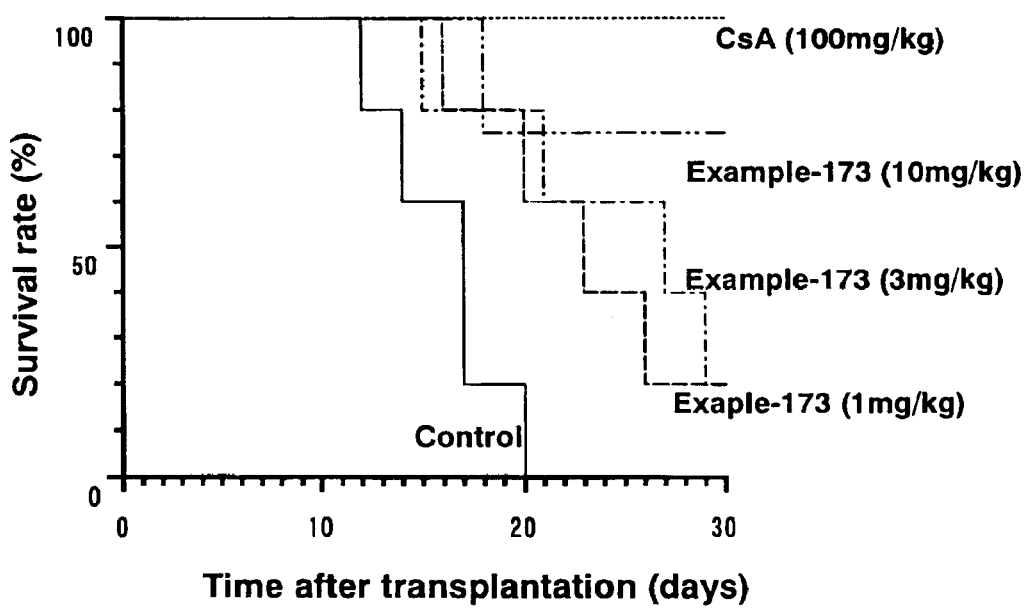
FIG. 8 is a graph showing activities of a test compound in a mouse skin graft model.

The results are shown in FIGS. 1 through 8.

As can be seen from the results, the compounds of the present invention represented by the general formula (1) have proven effective in animal model.

Industrial Applicability

As set forth, the present invention has been devised in recognition of the fact that novel diaryl derivatives, in particular those in which one of the aryl groups includes, at its para-position, a carbon chain with an aminopropanediol group and the other aryl group includes a substituent at its meta-position, exhibit strong immunosuppressive effects. Acting as effective immunosuppressors, the compounds of the present invention have a strong potential as a prophylactic or therapeutic agent against rejection in organ or bone marrow transplantation, autoimmune diseases, rheumatoid arthritis, psoriasis, atopic dermatitis, bronchial asthma, pollinosis and various other diseases.

What is claimed is:

1. A diaryl ether derivative, a pharmaceutically acceptable salt or hydrate thereof, the diaryl ether derivative represented by the following general formula (1):

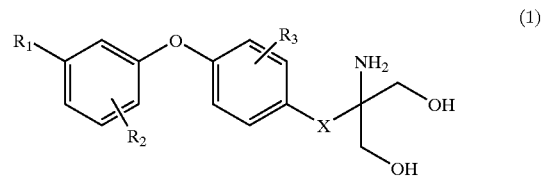

(1)

wherein $R_1$ is halogen, trihalomethyl, hydroxy, lower alkyl having 1 to 7 carbon atoms, phenyl, aralkyl, lower alkoxy having 1 to 4 carbon atoms, trifluoromethyloxy, substituted or unsubstituted phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

2. The diaryl ether derivative, pharmaceutically acceptable salt and hydrate thereof according to claim 1, wherein the compound of the general formula (1) is a compound represented by the following general formula (1a):

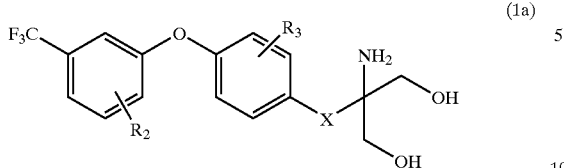

wherein $R_2$, $R_3$, and X are the same as defined above.

3. The diaryl ether derivative, pharmaceutically acceptable salt and hydrate thereof according to claim 2, wherein $R_3$ is fluorine.

4. The diaryl ether derivative, pharmaceutically acceptable salt and hydrate thereof according to claim 2, wherein $R_3$ is chlorine.

5. The diaryl ether derivative, pharmaceutically acceptable salt and hydrate thereof according to claim 2, wherein $R_3$ is trifluoromethyl.

6. The diaryl ether derivative, pharmaceutically acceptable salt and hydrate thereof according to claim 2, wherein X is —$(CH_2)_n$— (wherein n is an integer from 2 to 4).

7. The diaryl ether derivative, pharmaceutically acceptable salt and hydrate thereof according to claim 1, wherein the compound of the general formula (1) is a compound represented by the following general formula (1b):

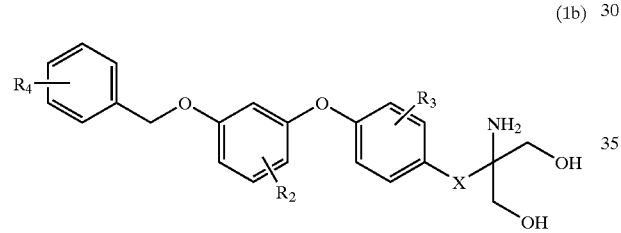

wherein $R_2$, $R_3$, and X are the same as defined above; and $R_4$ is hydrogen, halogen, trifluoromethyl, lower alkoxy having 1 to 4 carbon atoms, or lower alkyl having 1 to 7 carbon atoms.

8. The diaryl ether derivative, pharmaceutically acceptable salt and hydrate thereof according to claim 7, wherein $R_3$ is fluorine.

9. The diaryl ether derivative, pharmaceutically acceptable salt and hydrate thereof according to claim 2, wherein $R_3$ is chlorine.

10. The diaryl ether derivative, pharmaceutically acceptable salt and hydrate thereof according to claim 7, wherein $R_3$ is trifluoromethyl.

11. The diaryl ether derivative, pharmaceutically acceptable salt and hydrate thereof according to claim 7, wherein X is —$(CH_2)_n$— (wherein n is an integer from 2 to 4).

12. The diaryl ether derivative, pharmaceutically acceptable salt and hydrate thereof according to claim 1, wherein the compound of the general formula (1) is 1) 2-amino-2-[4-(3-benzyloxyphenoxy)-2-chlorophenyl] propyl-1,3-propanediol;
2) 2-amino-2-[4-(3-benzyloxyphenoxy)phenyl]propyl-1, 3-propanediol;
3) 2-amino-2-[4-(3-benzyloxyphenoxy)-2-chlorophenyl] ethyl-1,3-propanediol;
4) 2-amino-2-[4-(3-benzyloxyphenoxy)-2-chlorophenyl] butyl-1,3-propanediol;
5) 2-amino-2-[4-(3-(3',5'-dichlorobenzyloxy)phenoxy)-2-chlorophenyl]propyl-1,3-propanediol;
6) 2-amino-2-[4-(3-(3'-chlorobenzyloxy)phenoxy)-2-chlorophenyl]propyl-1,3-propanediol;
7) 2-amino-2-[4-(3-(3'-trifluoromethylbenzyloxy) phenoxy)-2-chlorophenyl]propyl-1,3-propanediol;
8) 2-amino-2-[4-(3-benzyloxyphenoxy)-2-trifluoromethylphenyl]propyl-1,3-propanediol;
9) 2-amino-2-[4-(3,5-bistrifluoromethylphenoxy)phenyl] propyl-1,3-propanediol;
10) 2-amino-2-[4-(3,5-bistrifluoromethyl-2-chlorophenoxy)phenyl]propyl-1,3-propanediol;
11) 2-amino-2-[4-(3,5-bistrifluoromethylphenoxy) phenyl]ethyl-1,3-propanediol;
12) 2-amino-2-[2-chloro-4-(3-trifluoromethylphenoxy) phenyl]propyl-1,3-propanediol;
13) 2-amino-2-[2-trifluoromethyl-4-(3-trifluoromethylphenoxy)phenyl]propyl-1,3-propanediol;
14) 2-amino-2-[4-(3,5-dichlorophenoxy)phenyl]propyl-1, 3-propanediol;
15) 2-amino-2-[4-(3-benzyloxy-5-trifluoromethylphenoxy)phenyl]propyl-1,3-propanediol; or
16) 2-amino-2-[2-fluoro-4-(3-trifluoromethylphenoxy) phenyl]propyl-1,3-propanediol.

13. An immunosuppressive agent containing as an active ingredient at least one of a diaryl ether derivative, a pharmaceutically acceptable salt and hydrate thereof, the diaryl ether derivative represented by the following general formula (1):

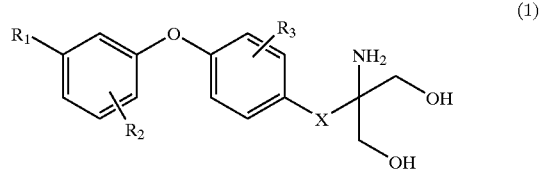

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —CH=$CHCH_2$—.

14. An immunosuppressive agent containing as an active ingredient at least one of the diaryl ether derivative, pharmaceutically acceptable salt and hydrate thereof according to claim 13, wherein the compound of the general formula (1) is a compound represented by the following general formula (1a):

(1a)

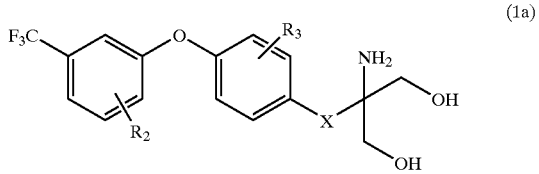

wherein $R_2$, $R_3$, and X are the same as defined above.

15. An immunosuppressive agent containing as an active ingredient at least one of the diaryl ether derivative, pharmaceutically acceptable salt and hydrate thereof according to claim 13, wherein the compound of the general formula (1) is a compound represented by the following general formula (1b):

(1b)

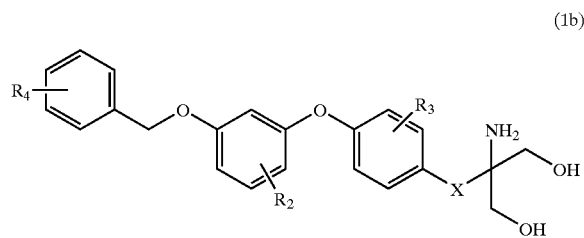

wherein $R_2$, $R_3$, and X are the same as defined above; and $R_4$ is hydrogen, halogen, trifluoromethyl, lower alkoxy having 1 to 4 carbon atoms, or lower alkyl having 1 to 7 carbon atoms.

16. A method for prophylactic or therapeutic inhibition of rejection in organ or bone marrow transplantation which comprises administering to a subject in need of same, an immunosuppressive agent containing as an active ingredient at least one of a diaryl ether derivative, a pharmaceutically acceptable salt and hydrate thereof, the diaryl ether derivative represented by the following general formula (1):

(1)

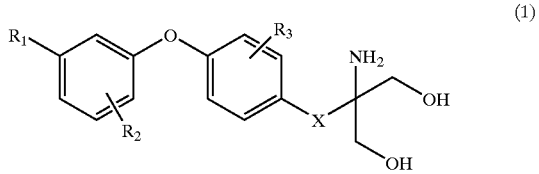

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

17. A method for prophylactic or therapeutic treatment of autoimmune diseases which comprises administering to a subject in need of same, an immunosuppressive agent containing as an active ingredient at least one of a diaryl ether derivative, a pharmaceutically acceptable salt and hydrate thereof, the diaryl ether derivative represented by the following general formula (1):

(1)

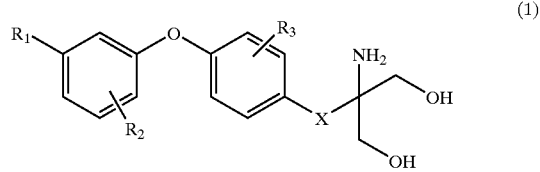

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

18. A method for prophylactic or therapeutic treatment of rheumatoid arthritis which comprises administering to a subject in need of same, an immunosuppressive agent containing as an active ingredient at least one of a diaryl ether derivative, a pharmaceutically acceptable salt and hydrate thereof, the diaryl ether derivative represented by the following general formula (1):

(1)

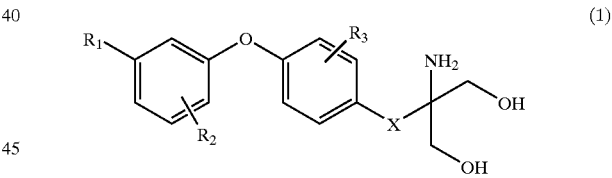

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

19. A method for prophylactic or therapeutic treatment of psoriasis or atopic dermatitis which comprises administering to a subject in need of same, an immunosuppressive agent containing as an active ingredient at least one of a diaryl ether derivative, a pharmaceutically acceptable salt and hydrate thereof, the diaryl ether derivative represented by the following general formula (1):

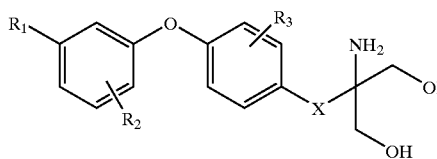

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

20. A method for prophylactic or therapeutic agent of bronchial asthma or pollinosis which comprises administering to a subject in need of same, an immunosuppressive agent containing as an active ingredient at least one of a diaryl ether derivative, a pharmaceutically acceptable salt and hydrate thereof, the diaryl ether derivative represented by the following general formula (1):

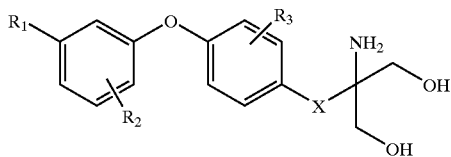

wherein $R_1$ is halogen, trihalomethyl, hydroxy, lower alkyl having 1 to 7 carbon atoms, substituted or unsubstituted phenyl, aralkyl, lower alkoxy having 1 to 4 carbon atoms, trifluoromethyloxy, phenoxy, cyclohexylmethyloxy, substituted or unsubstituted aralkyloxy, pyridylmethyloxy, cinnamyloxy, naphthylmethyloxy, phenoxymethyl, hydroxymethyl, hydroxyethyl, lower alkylthio having 1 to 4 carbon atoms, lower alkylsulfinyl having 1 to 4 carbon atoms, lower alkylsulfonyl having 1 to 4 carbon atoms, benzylthio, acetyl, nitro, or cyano; $R_2$ is hydrogen, halogen, trihalomethyl, lower alkoxy having 1 to 4 carbon atoms, lower alkyl having 1 to 7 carbon atoms, phenethyl, or benzyloxy; $R_3$ is hydrogen, halogen, trifluoromethyl, lower alkoxy having 1 to 4 carbon atoms, hydroxy, benzyloxy, lower alkyl having 1 to 7 carbon atoms, phenyl, lower alkoxymethyl having 1 to 4 carbon atoms, or lower alkylthio having 1 to 4 carbon atoms; and X is —$(CH_2)_n$— (n is an integer from 1 to 4), —$OCH_2CH_2$—, or —$CH=CHCH_2$—.

* * * * *